United States Patent [19]
Rutter et al.

[11] Patent Number: 4,462,821
[45] Date of Patent: Jul. 31, 1984

[54] SUBSTITUTED THIOSEMICARBAZIDES, THEIR MANUFACTURE AND USE AS PLANT GROWTH REGULANTS

[75] Inventors: Jerry L. Rutter, Overland Park; James L. Ahle, Shawnee, both of Kans.

[73] Assignee: Gulf Oil Corporation, Pittsburgh, Pa.

[21] Appl. No.: 239,938

[22] Filed: Mar. 2, 1981

Related U.S. Application Data

[60] Division of Ser. No. 62,258, Aug. 2, 1979, Pat. No. 4,282,031, which is a continuation-in-part of Ser. No. 942,232, Sep. 14, 1978, abandoned, and Ser. No. 000,851, Jan. 3, 1979, abandoned.

[51] Int. Cl.³ .................... A01N 33/26; C07C 101/26
[52] U.S. Cl. ........................................ 71/99; 544/160; 546/245; 548/539; 560/34; 562/439; 564/18
[58] Field of Search .............. 560/34; 71/99; 562/439

[56] References Cited

FOREIGN PATENT DOCUMENTS 53-74549 7/1978 Japan.
1272920 5/1972 United Kingdom.

OTHER PUBLICATIONS

Meran, Rev. Stiintifica, vol. 32 (1946), pp. 136–138.
Buu-Hoi et al., Bul. Soc. Chim. France (1965), 363–369.

Primary Examiner—Catherine L. Mills
Attorney, Agent, or Firm—Deane E. Keith; Forrest D. Stine

[57] ABSTRACT

The present invention is directed to a class of novel 1-benzoyl-3-thiosemicarbazides which are useful as plant growth regulants. The present invention is also directed to methods and formulations for plant growth regulation.

24 Claims, No Drawings

SUBSTITUTED THIOSEMICARBAZIDES, THEIR MANUFACTURE AND USE AS PLANT GROWTH REGULANTS

CROSS-REFERENCE TO RELATED APPLICATIONS

This is a division of application Ser. No. 62,258 filed Aug. 2, 1979, now U.S. Pat. No. 4,282,031 which is a continuation-in-part of U.S. Ser. No. 942,232 filed Sept. 14, 1978 abandoned, and U.S. Ser. No. 000,851 filed Jan. 3, 1979 abandoned, which are incorporated herein by reference.

BRIEF SUMMARY OF THE INVENTION

The present invention is directed to a class of novel 1-benzoyl-3-thiosemicarbazides which are useful as plant growth regulants. The present invention is also directed to methods and formulations for plant growth regulation.

DETAILED DESCRIPTION OF THE INVENTION

The present invention is directed to a class of novel 1-benzoyl-3-thiosemicarbazides of the formula I:

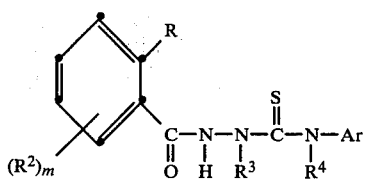

wherein
R is

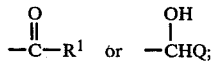

$R^1$ is —OH, —NR'R", $C_1$–$C_4$ alkyl or hydrogen;
Q is hydrogen or $C_1$–$C_4$ straight chain alkyl;
each of R' and R" independently is hydrogen or $C_1$–$C_{10}$ alkyl, $C_3$–$C_7$ alkoxyalkyl or alkoxyalkoxyalkyl, $C_3$–$C_6$ cycloalkyl, phenyl $C_1$–$C_2$ alkyl where the phenyl group is optionally mono-substituted by fluoro or methoxy, or R' and R" taken together with the nitrogen atom to which they are attached form a pyrrolidino, piperidino or morpholino ring;
each $R^2$ independently is chloro, fluoro, bromo, methyl, nitro or trifluoromethyl;
m is 0, 1 or 2;
$R^3$ is hydrogen, $C_1$–$C_4$ alkyl, $C_3$–$C_4$ alkenyl containing no α,β unsaturation, 2-hydroxyethyl, phenyl or benzyl;
$R^4$ is hydrogen or $C_1$–$C_3$ alkyl;
Ar is naphthyl, anthranyl, phenanthryl or a group having one of the following formulae:

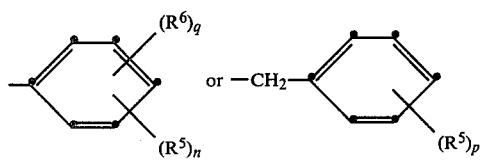

each $R^5$ independently is $C_1$–$C_4$ alkyl, chloro, bromo, fluoro, nitro, $C_1$–$C_3$ alkoxy or $C_1$–$C_3$ alkylthio, provided that both ortho positions are not substituted by alkyl;
$R^6$ is carbethoxy, phenoxy, benzyloxy, phenyl or dimethylamino;
n is 0, 1, 2 or 3;
q is 0 or 1;
the sum of n plus q does not exceed 3; and
p is 0 or 1;
or an agriculturally-acceptable salt or ester thereof.

The present invention is also directed to methods employing and formulations comprising the foregoing compounds for plant growth regulation.

SYNTHESIS OF THE COMPOUNDS

The compounds of the invention may be prepared by reacting a compound of formula II:

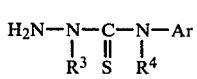

with a phthalic acid derivative of formula:

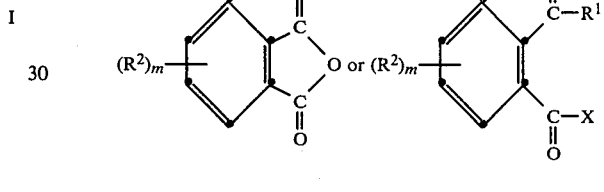

where $R^1$, $R^2$, $R^3$, $R^4$ and m are as defined above and where X is a good leaving group, preferably a halogen atom such as chlorine.

It is highly preferred that the above reaction be effected in a homogeneous system, i.e. be a uniphase reaction. Thus, an organic solvent is advantageously utilized which is capable of dissolving both reactants. Suitable organic solvents which may be mentioned are polar organic solvents such as chloroform, ethylene dichloride, isopropanol, dioxane, 1,2-dimethoxyethane and dimethylformamide and methylenedichloride.

The reaction is preferably effected without drastic heating, temperatures in the range from −40° to 100° C. generally being suitable—although the utilization of temperatures in the range from room temperature to 50° C. is preferred.

Many of the intermediates of formula II are believed to be novel.

Free acids of formula I (i.e. compounds in which $R^1$ is hydroxyl) may be converted to salts or esters. To effect salt formation the acid can be neutralized with any suitable base using conventional techniques. For instance, the potassium salt can be generated from the free acid by reaction with KOH in isopropanol. Generally, any suitable inert solvent capable of dissolving at least one of the reactants to an appreciable extent may be utilized. Preferred temperatures for the neutralization lie in the range of from −40° to 100° C., most preferably from room temperature to 50° C. As well as metal salts, ammonium and quaternary ammonium salts can be formed by the neutralization process, as can amine salts such as those formed with pyridine or diethylamine. The salts of the invention can also be formed by conventional double decomposition techniques.

The compounds of formula II in which $R^4$ is hydrogen can be prepared by reaction of the corresponding isothiocyanate of formula V:

       V and the corresponding hydrazine of formula:

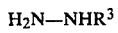

at a temperature from 0° to 50° C. in an inert organic solvent such as toluene capable of dissolving both reactants to an appreciable extent. This procedure is described in *Acta. Chemica. Scandinavica.*, 22 (1), 1, 1968. Compounds of formula II in which $R^4$ is not hydrogen can be prepared by reacting the corresponding N-alkyl-N-arylthiocarbamyl chloride of formula VI:

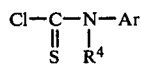       VI with a hydrazine of formula:

The reaction may be effected in inert organic solvents such as diethyl ether and at a temperature in the range from 0° to 50° C., preferably at room temperature.

Compounds of formula VI may be prepared by the general method described in *Chemical Abstracts*, 58, 4543, i.e. reaction of the corresponding amine of formula $ArNHR^4$ and thiophosgene in an ethereal solvent under anhydrous conditions at a temperature between 0° C. and room temperature.

Esters of formula I can be converted to other esters by methods well-known to those skilled in the art. For instance, ester exchange reactions may be accomplished by dissolving the ester in an excess of the alcohol with which exchange is desired. A small amount of base such as tertiary butylamine may be utilized to promote the reaction which is advantageously effected at temperatures in the range from −40° to 60° C. preferably from 0° to 50° C., most preferably at about room temperature.

Compounds of formula I in which $R^1$ is NR'R" can be prepared by reacting the corresponding methyl ester (R is COOMe) with the appropriate amine of formula HNR'R".

The methyl esters of formula I (i.e. R is COOMe) can also be used to prepare the corresponding hydroxymethyl (i.e. R is $CH_2OH$) compounds. Thus, the methyl esters can be reduced to the corresponding hydroxymethyl derivatives by treatment with chemical reducing agents such as sodium borohydride ($NaBH_4$). This reduction is preferably effected at a temperature in the range from 0° to 50° C., most preferably at 5° C. to room temperature. Suitable organic solvents which may be mentioned are the alkanolic solvents such as ethanol. Similarly, compounds of formula I in which R is —CHQOH where Q is $C_1$–$C_4$ alkyl can be prepared by reduction of the corresponding acyl derivatives (R is —$COR^1$ where $R^1$ is $C_1$–$C_4$ alkyl) using chemical reducing agents such as lithium aluminum hydride or sodium borohydride as above.

The following Preparations will serve to illustrate the preparation of intermediates of use in the invention. All temperatures are in degrees Celsius.

PREPARATION 1

Methyl hydrogen phthalate

Methanol (300 ml) was added in a single portion to 148 g (1.00 mole) of phthalic anhydride and the resulting suspension was stirred and heated at reflux for 36 hours; solution occurred during heating. The solvent was removed and the product was recrystallized from a mixture of ethyl acetate and hexane to afford 114.6 g of the title compound (Lit.: Beilstein, 9 797—m.p. 82.5°–84°).

PREPARATION 2

Methyl phthaloyl chloride

Methyl hydrogen phthalate (110.0 g, 0.611 mole) and thionyl chloride (77.4 g, 0.650 mole) were mixed in 200 ml of chloroform, keeping the temperature below 30°. After stirring for two hours at room temperature, the system was heated to reflux for five hours. The solvent was evaporated at reduced pressure and the crude product (120.9 g) was used without further purification (Lit.: Beilstein, 9 797—no constants).

PREPARATION 3

2,4-Dimethyl-4-phenyl-3-thiosemicarbazide

To a solution of N-methyl-N-phenylthiocarbamyl chloride (79.6 g, 0.43 mole) in 250 ml dry ether, a solution of 39.5 g (0.86 mole) methylhydrazine in 100 ml of dry ether was added dropwise with stirring below 10° C. The reaction temperature was allowed to increase to room temperature and the mixture was filtered. The filtrate was evaporated to low volume and diluted with about 300 ml hexane. After stirring for a few hours the hexane layer was decanted. The hexane immiscible layer was re-evaporated to remove organic solvents, giving the desired product, (70.0 g) as a thick orange liquid.

PREPARATION 4

4-Methyl-4-phenyl-3-thiosemicarbazide

To a solution of 7.7 g (0.24 mole) anhydrous hydrazine in 200 ml of dry ether, N-methyl-N-phenylthiocarbamyl chloride (20.4 g, 0.11 mole) was added below 5° C. with stirring. The mixture was stirred and allowed to warm to room temperature. The mixture was filtered and the residue resuspended in about 100 ml water and stirred. Filtration gave 8.8 g of the desired product as a whitish powder, m.p. 121°–22°.

PREPARATION 5

1-Amino-3-(2-naphthyl)thiourea

Anhydrous hydrazine (1.1 g, 0.035 mole) was dissolved in 150 ml of diethyl ether in a round-bottomed flask. 2-Naphthyl isothiocyanate (4.6 g, 0.25 mole) was added dropwise to the mixture keeping the pot temperature below 30° during the addition. The reaction mixture was stirred overnight at room temperature. The reactants were then cooled and the title product filtered off. The product was air-dried, yield 4.5 g, m.p. 174°–6°.

PREPARATION 6

2-Benzyl-4-phenyl-3-thiosemicarbazide

Benzylhydrazine (30 g, 0.0245 mole) and phenyl isothiocyanate (33.1 g, 0.0245 mole) were dissolved in 200 ml of isopropanol and cooled to 0°–5° C. The phenyl isothiocyanate was then added dropwise in 50 ml of petroleum ether. The title compound precipitated from solution during this phase of the operation. After addition, the reaction mixture was stirred at 40°–45° C. for one hour. The title product was filtered off as a white solid, m.p. 121°–3° C., yield 43 g.

The following Examples illustrate the preparation of compounds of formula I. All temperatures are in degrees Celsius.

EXAMPLE 1

1-(2-Carbomethoxybenzoyl)-2-methyl-4-phenyl-3-thiosemicarbazide

A solution of 45.3 g (0.25 mole) of 2-methyl-4-phenyl-3-thiosemicarbazide and 19.8 g (0.25 mole) of pyridine in 800 ml of 1,2-dimethoxyethane was stirred at room temperature while 49.8 g (0.25 mole) of methyl phthaloyl chloride in 100 ml of 1,2-dimethoxyethane was added dropwise over a period of two hours. The resulting reaction mixture was stirred for 16 hours at room temperature. At the end of this time the contents of the flask were poured into ice water. The solid which formed was collected and amounted to 73.3 g (85%); the melting point was 153.5°–154°.

EXAMPLE 2

1-(2-Carbomethoxybenzoyl)-2-isopropyl-4-phenyl-3-thiosemicarbazide

2-Isopropyl-4-phenyl-3-thiosemicarbazide (0.25 mole) prepared by reacting isopropylhydrazine with phenyl isothiocyanate according to the procedure of *Acta. Chem. Scand.* 22 (1), 1 (1968) and pyridine (0.25 mole) were dissolved in 125 ml of dimethoxyethane and placed in a 300 ml 3-necked flask equipped with funnel and thermometer. The contents were cooled to 10°–15° and methyl phthaloyl chloride (0.25 mole) in 25 ml of dimethoxyethane, added dropwise. The contents were then stirred overnight at room temperature. The following morning the contents were poured into ice water yielding the title product as a solid which was rinsed with hexane and ethyl acetate. No further purification was required. (m.p. 145°–147°), yield, 15.4 g

EXAMPLE 3

1-(2-Carbomethoxybenzoyl)-4-phenyl-3-thiosemicarbazide

The title compound was prepared by the procedure of Example 2. The resultant solid was rinsed with hexane and ethyl acetate and required no further purification. (m.p. 140°–142° C.) yield, 87%

EXAMPLE 4

1-(2-Carboxybenzoyl)-2-methyl-4-phenyl-3-thiosemicarbazide

2-Methyl-4-phenyl-3-thiosemicarbazide (0.2 mole) was dissolved in about 75 ml of dimethylformamide and placed in a 3-necked round-bottomed flask equipped with magnetic stirrer, condenser, additional powder funnel and thermometer. Phthalic anhydride (0.2 mole) was added in portions at 20°. The contents were stirred overnight at room temperature, then poured into ice water the following morning. The resulting solid title product was recrystallized from a mixture of hexane and ethanol. (m.p. 155°–156°) yield, 70%

EXAMPLE 5

1-(2-Carboxybenzoyl)-4-phenyl-3-thiosemicarbazide

The same apparatus and procedure were used as in Example 4. After all the phthalic anhydride was added the contents were heated at 80° for about 3 hours. The contents were then cooled and poured into ice water resulting in production of the title compound as a solid. This solid was rinsed with a mixture of hexane and ethanol. (m.p. 149°–151°) yield, 66%

EXAMPLE 6

1-(2-Carboxybenzoyl)-2-methyl-4-phenyl-3-thiosemicarbazide, sodium salt

The free acid of Example 4 was suspended in methanol and placed in a 300 ml round-bottomed flask equipped with magnetic stirrer and condenser. Sodium methoxide was suspended in methanol and added to the reaction flask. The reaction mixture was stirred at room temperature for 30 minutes during which time all solids went into solution. The contents were then evaporated, yielding the title product. Yield, 7.6 g, m.p. 195°–197° (dec.)

EXAMPLE 7

1-(2-Carboxybenzoyl)-2-methyl-4-phenyl-3-thiosemicarbazide, ammonium salt

The free acid compound of Example 4 was suspended in 100 ml of ethanol and placed in a 300 ml round-bottomed flask equipped with magnetic stirrer and condenser. Twenty ml of dimethoxyethane were added to make the compound go into solution. After most of the solid had gone into solution, NH4OH was added. There was no discernible heat evolution. Solvents were evaporated. The resulting solid (title product) was refluxed in a mixture of hexane and ethanol and was then recovered by filtration. Yield 4.3 g (m.p. 165°–166°)

EXAMPLE 8

1-(2-Carboisopropoxybenzoyl)-2-methyl-4-phenyl-3-thiosemicarbazide

To a solution of 5.0 g (0.014 mole) of 1-(2-carbomethoxybenzoyl)-2-methyl-4-phenyl-3-thiosemicarbazide in 75 ml of isopropyl alcohol was added 1.0 g (0.014 mole) of tert-butylamine and the solution was stirred at room temperature for 16–18 hours. Most of the isopropyl alcohol was removed at reduced pressure, and water was added and the resulting precipitate was collected. The title compound thus produced had a melting point of 115°–117°.

EXAMPLE 9

2-Benzyl-1-(2-carboxybenzoyl)-4-phenyl-3-thiosemicarbazide

Phthalic anhydride (3.7 g, 0.25 mole) and 2-benzyl-4-phenyl-3-thiosemicarbazide (6.43 g, 0.25 mole) were dissolved in 100 ml of dimethylformamide and heated at 90° C. for three hours. The solution was cooled then poured into ice water with stirring. The title product was filtered off as a solid material. Recrystallization gave a substance having a melting point of 140°–142°.

EXAMPLE 10

1-(2-Carboxybenzoyl)-2-methyl-4-phenyl-3-thiosemicarbazide, potassium salt 1-(2-Carboxybenzoyl)-2-methyl-4-phenyl-3-thiosemicarbazide (60 g, 0.182 mole) was dissolved (slurried) in 400 ml ethanol. Potassium hydroxide (10.2 g) was dissolved in 200 ml ethanol and added to the acid-ethanol mixture. Ethanol was evaporated until a crystalline product precipitated, yield 51 g and m.p. 182°–183°.

EXAMPLE 11

1-(2-Dimethylaminocarbonylbenzoyl)-2-methyl-4-phenyl-3-thiosemicarbazide 1-(2-Carbomethoxybenzoyl)-2-methyl-4-phenyl-3-thiosemicarbazide (5 g, 0.148 mole) was suspended in aqueous dimethylamine. The pH of the suspension was adjusted to about 3. A tacky precipitate was formed which become solid after addition of diethyl ether. This solid—title product—had a melting point of 140°–143°, yield 3.7 g.

EXAMPLE 12

1-(2-Hydroxymethylbenzoyl)-2-methyl-4-(3-fluorophenyl)-3-thiosemicarbazide 1-(2-Carbomethoxybenzoyl)-2-methyl-4-(3-fluorophenyl)-3-thiosemicarbazide (7.2 g) was dissolved in ethanol (100 ml). The solution was cooled to below 10° and sodium borohydride (1.1 g) added. The mixture was then stirred at room temperature for 60 hours. Water was then added with production of an amorphous precipitate. Dilute hydrochloric acid was then added to the filtrate to bring it to pH 7 and further precipitate removed by filtration. The filtrate was thereupon acidified to yield the title product as a solid, m.p. 136°–137°, yield 3.4 g.

Using the foregoing procedures a large number of other compounds of formula I were prepared. These compounds, as well as the compounds prepared by the processes of Examples 1 to 12, are listed in the following Table I.

TABLE I

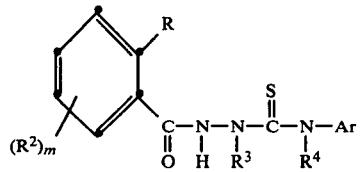

| Compound No. | R | m | $R^2$ | $R^3$ | $R^4$ | Ar | M.P. °C. |
|---|---|---|---|---|---|---|---|
| 597 | —COOCH$_3$ | 0 | — | —CH$_3$ | —H | phenyl | 153.5–154° |
| 1685 | —COOCH$_3$ | " | — | —CH(CH$_3$)$_2$ | —H | phenyl | 145–147° |
| 1686 | —COOCH$_3$ | " | — | —H | —H | phenyl | 140–142° |
| 2005 | —COOH | " | — | —CH$_3$ | —H | phenyl | 155–156° |
| 2008 | —COOH | " | — | —H | —H | phenyl | 149–151° |
| 2044 | —COONa | " | — | —CH$_3$ | —H | phenyl | High melt solid |
| 2047 | —COONH$_4$ | " | — | —CH$_3$ | —H | phenyl | 165–166° |
| 2322 | —COOCH$_3$ | " | — | —CH$_3$ | —H | benzyl | 144–146° |
| 2324 | —COOCH$_3$ | " | — | —H | —H | benzyl | 133–135° |
| 2325 | —COOCH$_3$ | " | — | —CH$_3$ | —H | 4-methylphenyl | 138–140° |
| 2341 | —COONa | " | — | —H | —H | benzyl | High melt solid |
| 2342 | —COONH$_4$ | " | — | —H | —H | benzyl | 173–175° |
| 2370 | —COOCH$_2$CH$_2$CH$_3$ | " | — | —CH$_3$ | —H | phenyl | 117–119° |
| 2371 | —COOCH$_2$CH$_3$ | " | — | —CH$_3$ | —H | phenyl | 142–145° |
| 2372 | —COO(CH$_2$)$_3$CH$_3$ | " | — | —CH$_3$ | —H | phenyl | 98–100° |
| 2388 | —COOCH$_3$ | " | — | —CH$_3$ | —H | 3-chloro-4-methylphenyl | 142–146° |
| 2389 | —COOCH$_3$ | " | — | —CH$_3$ | —H | 3-methylphenyl | 138–140° |
| 2390 | —COOCH$_3$ | " | — | —CH$_3$ | —H | 3-methoxyphenyl | 142–144° |
| 2391 | —COOCH$_3$ | " | — | —CH$_3$ | —H | 2-fluorophenyl | 152–154° |
| 2392 | —COOCH$_3$ | " | — | —CH$_3$ | —H | 4-fluoro-2-methylphenyl | 127–129° |
| 2414 | —COOCH$_2$CH$_2$Cl | " | — | —CH$_3$ | —H | phenyl | 126–131° |
| 2415 | —COO(CH$_2$)$_6$Cl | " | — | —CH$_3$ | —H | phenyl | oil |
| 2418 | —COOH | " | — | benzyl | —H | phenyl | 140–142° |
| 2422 | —COOCH$_3$ | " | — | benzyl | —H | phenyl | 103–106° |
| 2432 | —COOH | 1 | 3-CH$_3$ | —CH$_3$ | —H | phenyl | 123–126° |
| 2433 | —COOH | " | 3-CH$_3$ | —H | —H | phenyl | 122–123° |
| 2434 | —COONH$_4$ | " | 3-CH$_3$ | —CH$_3$ | —H | phenyl | 154–157° |
| 2444 | —COO(CH$_2$)$_4$CH$_3$ | 0 | — | —CH$_3$ | —H | phenyl | 131–133° |
| 2445 | —COOCH$_2$CH$_2$CHCH$_3$ with CH$_3$ branch | " | — | —CH$_3$ | —H | phenyl | 126–129° |

TABLE I-continued

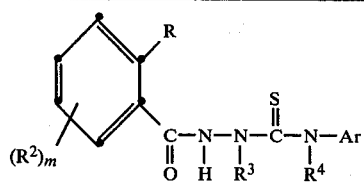

| Compound No. | R | m | $R^2$ | $R^3$ | $R^4$ | Ar | M.P. °C. |
|---|---|---|---|---|---|---|---|
| 2446 | —COO(CH$_2$)$_5$CH$_3$ | " | — | —CH$_3$ | —H | phenyl | 113–117° |
| 2450 | —COOH | 1 | 6-NO$_2$ | —CH$_3$ | —H | phenyl | 160–163° |
| 2470 | —CONH$_2$ | 0 | — | —CH$_3$ | —H | phenyl | 161–163° |
| 2472 | —CON(CH$_3$)$_2$ | " | — | —CH$_3$ | —H | phenyl | 140–143° |
| 2474 | —COOH | " | — | —CH$_3$ | —H | 4-chlorophenyl | 165–166° |
| 2479 | —COOH | " | — | —CH$_3$ | —H | benzyl | 161–163° |
| 2480 | —COOH | " | — | —H | —H | benzyl | 183–184° |
| 2481 | —COOH | " | — | —CH$_3$ | —H | 4-methylphenyl | 156–158° |
| 2482 | —COOH | " | — | —CH$_3$ | —H | 3-methylphenyl | 133–135° |
| 2483 | —COOH | " | — | —CH$_3$ | —H | 2-fluorophenyl | 137–139° |
| 2484 | —COOH | " | — | —CH$_3$ | —H | 4-fluoro-2-methylphenyl | 158–161° |
| 2487 | —COOH | " | — | —CH$_3$ | —H | 4-fluorophenyl | 167–168° |
| 2488 | —COOH | " | — | —CH$_3$ | —H | 3-fluorophenyl | 165–166° |
| 2563 | —COOCH$_3$ | " | — | —CH$_3$ | —H | 2-chlorophenyl | 151–153° |
| 2564 | —COOCH$_3$ | " | — | —CH$_3$ | —H | 2-nitrophenyl | 171–173° |
| 2567 | —COOCH$_3$ | " | — | —CH$_3$ | —H | 4-fluorophenyl | 149–151° |
| 2568 | —COOCH$_3$ | " | — | —CH$_3$ | —H | 3-fluorophenyl | 146–148° |
| 2569 | —COOCH$_3$ | " | — | —CH$_3$ | —H | 4-chlorophenyl | 159–161° |
| 2570 | —COOCH$_3$ | " | — | —CH$_3$ | —H | 3-chlorophenyl | 143–145° |
| 2571 | —COOCH$_3$ | " | — | —CH$_3$ | —H | 4-nitrophenyl | 195–197° |
| 2572 | —COOCH$_3$ | " | — | —CH$_3$ | —H | 3-(trifluoromethyl)phenyl | 141–143° |
| 2573 | —COOCH$_3$ | " | — | —H | —H | 3-methoxyphenyl | 132–134° |
| 2574 | —COOCH$_3$ | " | — | —H | —H | 3-chloromethylphenyl | 155–158° |
| 2576 | —COOCH$_3$ | " | — | —H | —H | 2-nitrophenyl | 144–146° |
| 2577 | —COOCH$_3$ | " | — | —H | —H | 3-methylphenyl | 138–140° |
| 2578 | —COOCH$_3$ | " | — | —H | —H | 2-chlorophenyl | 149–151° |
| 2579 | —COOCH$_3$ | " | — | —CH$_3$ | —H | 2-naphthyl | 135–137° |
| 2580 | —COOCH$_3$ | " | — | —H | —H | 2-fluorophenyl | 151–153° |
| 2581 | —COOCH$_3$ | " | — | —H | —H | 4-fluorophenyl | 163–165° |
| 2583 | —COOCH$_3$ | " | — | —H | —H | 4-methylphenyl | 151–153° |
| 2584 | —COOCH$_3$ | " | — | —H | —H | 3-fluorophenyl | 158–160° |
| 2585 | —COOCH$_3$ | " | — | —H | —H | 4-chlorophenyl | 162–164° |
| 2586 | —COOCH$_3$ | " | — | —H | —H | 3-chlorophenyl | 153–155° |
| 2588 | —COOCH$_3$ | " | — | —H | —H | 3-(trifluoromethyl)phenyl | 161–163° |
| 2589 | —COOCH$_3$ | " | — | —H | —H | 1-naphthyl | 146–148° |
| 2590 | —COOCH$_3$ | " | — | —H | —H | 2-naphthyl | 148–150° |

TABLE I-continued

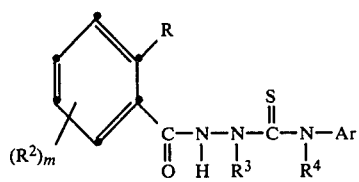

| Compound No. | R | m | R² | R³ | R⁴ | Ar | M.P. °C. |
|---|---|---|---|---|---|---|---|
| 2591 | —COOH | " | — | —CH₃ | —H | 3-chlorophenyl | 157–158° |
| 2592 | —COOH | " | — | —CH₃ | —H | 4-nitrophenyl | 200° |
| 2594 | —COOH | " | — | —CH₃ | —H | 1-naphthyl | 159–160° |
| 2595 | —COOH | " | — | —CH₃ | —H | 2-naphthyl | 112–114° |
| 2597 | —COOH | " | — | —CH₃ | —H | 3-(trifluoromethyl)-phenyl | 155–156° |
| 2598 | —COOH | " | — | —H | —H | 3-methoxyphenyl | 150–152° |
| 2599 | —COOH | " | — | —H | —H | 3-chloro-4-methylphenyl | 178–183° |
| 2603 | —COOH | " | — | —H | —H | 2-nitrophenyl | 170–171° |
| 2604 | —COOH | " | — | —H | —H | 3-methylphenyl | 169–170° |
| 2605 | —COOH | " | — | —H | —H | 2-chlorophenyl | 165–167° |
| 2622 | —COO(CH₂)₁₁CH₃ | " | — | —CH₃ | —H | phenyl | oil |
| 2627 | —COO(CH₂)₁₀CH₃ | " | — | —CH₃ | —H | phenyl | oil |
| 2628 | —COO(CH₂)₁₅CH₃ | " | — | —CH₃ | —H | phenyl | oil |
| 2633 | —COOCH₂CH₂—O—CH₂CH₃ | " | — | —CH₃ | —H | phenyl | oil |
| 2634 | —COOCH₂CH(C₂H₅)—(CH₂)₃CH₃ | " | — | —CH₃ | —H | phenyl | oil |
| 2635 | —COOCH₂CH₂—O—(CH₂)₃CH₃ | " | — | —CH₃ | —H | phenyl | oil |
| 2636 | —COOC₂H₄—O—C₂H₄—O—C₄H₉ | " | — | —CH₃ | —H | phenyl | oil |
| 2637 | —COOCH₂—C—(CH₃)₃ | " | — | —CH₃ | —H | phenyl | oil |
| 2641 | —COOH | " | — | —CH₂CH=CH₂ | —H | phenyl | 105–125° |
| 2668 | —COOC₂H₄—O—C₂H₄—O—C₂H₅ | " | — | —CH₃ | —H | phenyl | oil |
| 2669 | —COOCH₂CH₂—⌬ | " | — | —CH₃ | —H | phenyl | 131–133° |
| 2697 | —COOH | " | — | —H | —H | 2-naphthyl | 171–174° |
| 2698 | —COOH | " | — | —H | —H | 1-naphthyl | 158–159° |
| 2699 | —COOH | " | — | —H | —H | 3-(trifluoromethyl)-phenyl | 167–170° |
| 2700 | —COOH | " | — | —H | —H | 4-nitrophenyl | 298–302° |

TABLE I-continued

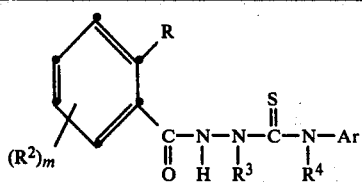

| Compound No. | R | m | $R^2$ | $R^3$ | $R^4$ | Ar | M.P. °C. |
|---|---|---|---|---|---|---|---|
| 2701 | —COOH | " | — | —H | —H | 3-chlorophenyl | 169–170° |
| 2702 | —COOH | " | — | —H | —H | 4-chlorophenyl | 187–189° |
| 2704 | —COOH | " | — | —H | —H | 3-fluorophenyl | 167–168° |
| 2705 | —COOH | " | — | —H | —H | 4-methylphenyl | 164–166° |
| 2707 | —COOH | " | — | —H | —H | 4-fluorophenyl | 179–181° |
| 2708 | —COOH | " | — | —H | —H | 2-fluorophenyl | 170–171° |
| 2721 | —COOH | " | — | —$CH_3$ | —H | 3,4-dichlorophenyl | 165–166° |
| 2722 | —COOH | " | — | —$CH_3$ | —H | 4-methoxyphenyl | 168–170° |
| 2723 | —COOH | " | — | —$CH_3$ | —H | 2-methylphenyl | 173–180° |
| 2724 | —COOH | " | — | —$CH_3$ | —H | 4-bromophenyl | 175–176° |
| 2725 | —COOH | " | — | —H | —H | 3,4-dichlorophenyl | 178–179° |
| 2726 | —COOH | " | — | —H | —H | 4-methoxyphenyl | 198–201° |
| 2727 | —COOH | " | — | —H | —H | 2-methylphenyl | 179–180° |
| 2728 | —COOH | " | — | —H | —H | 4-bromophenyl | 178–181° |
| 2729 | —COO($CH_2$)$_{11}$—$CH_3$ | " | — | —H | —H | phenyl | crude solid |
| 2732 | —COO($CH_2$)$_{10}$—$CH_3$ | " | — | —H | —H | 3-fluorophenyl | crude solid |
| 2733 | —COO($CH_2$)$_{15}CH_3$ | " | — | —H | —H | phenyl | crude solid |
| 2734 | —COO($CH_2$)$_{15}CH_3$ | " | — | —$CH_3$ | —H | 3-fluorophenyl | oil |
| 2735 | —COO($CH_2$)$_{15}CH_3$ | " | — | —$CH_3$ | —H | 4-fluorophenyl | crude solid |
| 2736 | —COO($CH_2$)$_{15}CH_3$ | " | — | —$CH_3$ | —H | 4-chlorophenyl | crude solid |
| 2740 | —COO$C_2H_4$—O—$C_4H_9$ | " | — | —$CH_3$ | —H | 3-fluorophenyl | crude solid |
| 2741 | —COO$C_2H_4$—O—$C_4H_9$ | " | — | —$CH_3$ | —H | 4-fluorophenyl | crude solid |
| 2742 | —COO$C_2H_4$—O—$C_4H_9$ | " | — | —$CH_3$ | —H | 4-chlorophenyl | crude solid |
| 2743 | —COO($CH_2$)$_9CH_3$ | " | — | —$CH_3$ | —H | phenyl | oil |
| 2744 | —COO($CH_2$)$_{17}CH_3$ | " | — | —$CH_3$ | —H | phenyl | gum |
| 2745 | —COOCH$_2$CH$_2$—Br | " | — | —$CH_3$ | —H | phenyl | gum |
| 2746 | —COO($CH_2$)$_7CH_3$ | " | — | —H | —H | phenyl | 117–121° |
| 2749 | —COO($CH_2$)$_9CH_3$ | " | — | —H | —H | phenyl | 103–105° |
| 2750 | —COOCH$_2$CH$_3$ | " | — | —H | —H | phenyl | 148–150° |
| 2753 | —COOH | 1 | 5-$CH_3$ | —$CH_3$ | —H | phenyl | 131–132° |
| 2754 | —COOH | " | 5-$CH_3$ | —H | —H | phenyl | 137–139° |
| 2756 | —COOCH$_3$ | " | 6-$NO_2$ | —$CH_3$ | —H | phenyl | 130–135° |
| 2760 | —COOCH$_3$ | " | 5-$CH_3$ | —H | —H | phenyl | 111–113° |
| 2762 | —COONH$_4$ | " | 5-$CH_3$ | —H | —H | phenyl | 170–172° |
| 2771 | —COONH$_4$ | " | 6-$CH_3$ | —$CH_3$ | —H | phenyl | 102° (0) |
| 2772 | —COOH | " | 5-$NO_2$ | —$CH_3$ | —H | phenyl | 123–124° |
| 2777 | —COO$C_2H_4$—O—$C_2H_4$—O—$C_2H_5$ | " | — | —H | —H | phenyl | 119–124° |

TABLE I-continued $$\underset{(R^2)_m}{\text{[structure]}} \quad \overset{R}{\underset{O\ H\ R^3\ R^4}{C-N-N-C-N-Ar}} \overset{S}{\underset{}{}}$$

| Compound No. | R | m | R² | R³ | R⁴ | Ar | M.P. °C. |
|---|---|---|---|---|---|---|---|
| 2778 | —COOCH₂CH₂— (furan) | " | — | —H | —H | phenyl | crude solid |
| 2779 | —COOC₂H₄—O— / —C₂H₄—O—C₄H₉ | 0 | — | —H | —H | phenyl | crude solid |
| 2781 | —COOC₂H₄—O—CH₃ | " | — | —H | —H | phenyl | crude solid |
| 2783 | —COOC₃H₆—Br | " | — | —H | —H | phenyl | 72-75° |
| 2784 | —COOH | 1 | 3-F | —CH₃ | —H | phenyl | 134-136° |
| 2787 | —COOH | " | 3-F | —H | —H | phenyl | 149-150° |
| 2788 | —COOH | 0 | — | —CH₂CH₃ | —H | phenyl | 153-155° |
| 2790 | —COOH, pyridine salt | " | — | —CH₃ | —H | phenyl | 126-129° |
| 2795 | —COOH | " | — | —H | —CH₃ | phenyl | 168° |
| 2796 | —COOCH₃ | " | — | —H | —CH₃ | phenyl | 95-99° |
| 2798 | —COOCH₃ | " | — | —CH₃ | —CH₃ | phenyl | 105-106° |
| 2799 | —COOCH₃ | " | — | —H | —H | 3,4-dichlorophenyl | 155-157° |
| 2800 | —COOCH₃ | " | — | —H | —H | 4-methoxyphenyl | 149-151° |
| 2801 | —COOCH₃ | " | — | —H | —H | 2-methylphenyl | 175-177° |
| 2802 | —COOCH₃ | " | — | —H | —H | 4-bromophenyl | 163-165° |
| 2803 | —COOCH₃ | " | — | —CH₃ | —H | 4-methoxyphenyl | 126-128° |
| 2818 | —COOH | 1 | 5-chloro | —CH₃ | —H | phenyl | 125-127° |
| 2819 | —COOH | " | 5-chloro | —H | —H | phenyl | 280-283° |
| 2822 | —COOCH₃ | 0 | — | —C₂H₅ | —H | phenyl | 166-168° |
| 2844 | —COOH, triethylenediamine salt | " | — | —CH₃ | —H | phenyl | 189-190° |
| 2845 | —COOK | " | — | —CH₃ | —H | phenyl | 181-183° |
| 2850 | —COOH | 2 | 4,5-dichloro | —CH₃ | —H | phenyl | 320-323° |
| 2851 | —COOH | " | 4,5-dichloro | —H | —H | phenyl | 158-159° |
| 2852 | —COONH₄ | " | 4,5-dichloro | —H | —H | phenyl | 170° (dec.) |
| 2853 | —COONH₄ | " | 4,5-dichloro | —CH₃ | —H | phenyl | 112-115° |
| 2854 | —COOLi | 0 | — | —CH₃ | —H | phenyl | — |
| 2855 | —COOH | 1 | 3-Br | —CH₃ | —H | phenyl | gum |
| 2859 | —COONH₄ | " | 6-F | —CH₃ | —H | phenyl | 163-165° |
| 2862 | —COONH₄ | " | 6-F | —H | —H | phenyl | 180° (dec.) |
| 2863 | —COOH | 2 | 3,6-dichloro | —CH₃ | —H | phenyl | 116-117° |
| 2879 | —COOCH₃ | 0 | — | —CH₃ | —H | 2,4-dimethylphenyl | 155-157° |
| 2882 | —COOH, dimethylmorpholinium salt | " | — | —CH₃ | —H | phenyl | 137-139° |
| 2883 | —COOH, salt with 4H-pyrido[1,2-α]pyrazine | " | — | —CH₃ | —H | phenyl | 168-170° |
| 2885 | —COOH, salt with diethylamine | " | — | —CH₃ | —H | phenyl | 147-149° |
| 2896 | —COOH | " | — | —CH₃ | —H | 2,4-di- | 172-178° |

TABLE I-continued

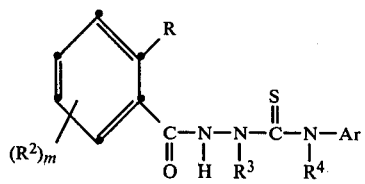

| Compound No. | R | m | R² | R³ | R⁴ | Ar | M.P. °C. |
|---|---|---|---|---|---|---|---|
| 2898 | —COONH₄ | 1 | 5-nitro | —CH₃ | —H | methylphenyl phenyl | 144–145° |
| 2914 | —COOH | 0 | — | —CH₃ | —CH₃ | phenyl | oil |
| 2923 | —COOH | 1 | 6-CF₃ | —CH₃ | —H | phenyl | 68–74° |
| 2954 | —COOH | 0 | — | -phenyl | —H | phenyl | 151° (dec.) |
| 2987 | —COOH | 1 | 4-nitro | —CH₃ | —CH₃ | phenyl | 83–90° |
| 2992 | —COOCH₃ | 0 | — | —CH₃ | —H | 2-carbethoxyphenyl | 120–122° |
| 2994 | —COOCH₃ | " | — | —CH₃ | —H | 4-phenoxyphenyl | 163–165° |
| 2995 | —COOCH₃ | " | — | —CH₃ | —H | 4-butylphenyl | 143–145° |
| 2996 | —COOCH₃ | " | — | —CH₃ | —H | 3-(methylthio)phenyl | 97–99° |
| 2997 | —COOCH₃ | " | — | —CH₃ | —H | 4-benzyloxyphenyl | 162–164° |
| 2998 | —COOCH₃ | " | — | —CH₃ | —H | 4-dimethylaminophenyl | 138–140° |
| 2999 | —COOCH₃ | " | — | —CH₃ | —H | 4-methylbenzyl | 147–149° |
| 3000 | —COOCH₃ | " | — | —CH₃ | —H | 2,6-dichlorophenyl | 162–164° |
| 3001 | —COOCH₃ | " | — | —CH₃ | —H | 4-carbethoxyphenyl | 142–144° |
| 3002 | —COOCH₃ | " | — | —CH₃ | —H | 4-isopropylphenyl | 156–158° |
| 3006 | —COOH | " | — | —CH₃ | —H | 2-carbethoxyphenyl | 158–159° |
| 3017 | —COOH | " | — | —CH₃ | —H | 4-phenoxyphenyl | 140–142° |
| 3018 | —COOH | " | — | —CH₃ | —H | 4-butylphenyl | 134–135° |
| 3019 | —COOH | " | — | —CH₃ | —H | 3-(methylthio)phenyl | glassy solid |
| 3022 | —COOH | " | — | —CH₃ | —H | 4-isopropylphenyl | 116–118° |
| 3023 | —COOH | " | — | —CH₃ | —H | 4-benzyloxyphenyl | 138–139° |
| 3024 | —COOH | " | — | —CH₃ | —H | 4-(dimethylamino)phenyl | 163–165° |
| 3025 | —COOH | " | — | —CH₃ | —H | 4-methylbenzyl | 157–158° |
| 3026 | —COOH | " | — | —CH₃ | —H | 4-carbethoxyphenyl | 160–161° |
| 3027 | —COOH | " | — | —CH₃ | —H | 2,6-dichlorophenyl | 156–157° |
| 3108 | —COOK | " | — | —CH₃ | —H | 3-fluorophenyl | 184–185° |
| 3109 | —COONH₄ | " | — | —CH₃ | —H | 3-fluorophenyl | 155–157° |
| 3116 | —COCH₃ | " | — | —CH₃ | —H | phenyl | oil |
| 3137 | —CO-1-piperidyl | " | — | —CH₃ | —H | phenyl | 150–152° |
| 3146 | —COOH, octylamine salt | " | — | —CH₃ | —H | phenyl | 133-14 135° |
| 3147 | —COOH | " | — | —CH₂CH₂OH | —H | phenyl | 155–157° |
| 3151 | —COOH | " | — | —CH₃ | —H | 2,3-dimethylphenyl | 118–120° |
| 3152 | —COOH | " | — | —CH₃ | —H | 2,4,5- | 160° (re- |

TABLE I-continued

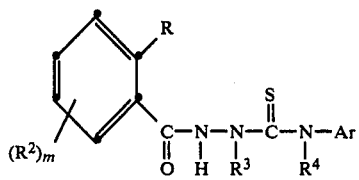

| Compound No. | R | m | R² | R³ | R⁴ | Ar | M.P. °C. |
|---|---|---|---|---|---|---|---|
| | | | | | | trimethyl-phenyl | arranges) |
| 3153 | —COOH | " | — | —CH₃ | —H | 2,5-di-methyl-phenyl | 130° (re-arranges) |
| 3158 | —COOH | " | — | —CH₃ | —H | 3,5-di methyl-phenyl | 107–110° |
| 3159 | —COOH | " | — | —CH₃ | —H | 3-ethyl-phenyl | unpurified |
| 3160 | —COOH | " | — | —CH₃ | —H | 3,4-di-methyl-phenyl | 126–128° |
| 3180 | —COOH, salt with benzyl-dimethylamine | " | — | —CH₃ | —H | phenyl | 68–85° |
| 3181 | —COOH, salt with phenyl-dimethylamine | " | — | —CH₃ | —H | phenyl | 145–147° (dec.) |
| 3182 | —COOH, salt with (2,3-dihydroxy-propyl)di-methylamine | " | — | —CH₃ | —H | phenyl | 139–141° (dec.) |
| 3183 | —COOH, salt with tri-octylamine | " | — | —CH₃ | —H | phenyl | oil |
| 3184 | —COOCH₃ | " | — | —CH₂CH₂OH | —H | phenyl | 147–149° |
| 3185 | —COOCH₃ | " | — | —CH₃ | —H | 2,3-di-methyl-phenyl | 136–138° |
| 3186 | —COOCH₃ | " | — | —CH₃ | —H | 2,4,5-tri-methyl-phenyl | 150–152° |
| 3187 | —COOCH₃ | " | — | —CH₃ | —H | 2,5-di-methyl-phenyl | 146–147° |
| 3194 | —COOCH₃ | " | — | —CH₃ | —H | 3,4-di-methyl-phenyl | 142–144° |
| 3195 | —COOCH₃ | " | — | —CH₃ | —H | 3,5-di-methyl-phenyl | 153–155° |
| 3196 | —COOCH₃ | " | — | —CH₃ | —H | 3-ethyl-phenyl | 78–81° |
| 3210 | —COOH, tetrahydro-furan adduct | " | — | —CH₃ | —H | phenyl | 155–158° |
| 3284 | —CONHC(CH₃)₃ | " | — | —CH₃ | —H | phenyl | 141–142° |
| 3285 | —CONHCH₂CH₂CH₃ | " | — | —CH₃ | —H | phenyl | 144–148° |
| 3290 | —CONHCH—CH₂CH₃<br>        \|<br>       CH₃ | " | — | —CH₃ | —H | phenyl | unpurified |
| 3349 | —COOCH₃ | " | — | —CH₃ | —H | 4-bromo-phenyl | 156–159° |
| 3350 | —COOCH₃ | " | — | —CH₃ | —H | 3-nitro-phenyl | 178–180° |
| 3352 | —COOCH₃ | " | — | —CH₃ | —H | 3,4-di-chloro-phenyl | 159–161° |
| 3358 | —COOCH—CH₃<br>       \|<br>      CH₃ | " | — | —CH₃ | —H | phenyl | 115–117° |
| 3577 | (—COO)₂Ca | " | — | —CH₃ | —H | phenyl | >300° |
| 3578 | (—COO)₂Zn | " | — | —CH₃ | —H | phenyl | 170–175° (dec.) |
| 3579 | (—COO)₂Cu | " | — | —CH₃ | —H | phenyl | 150–153° (dec.) |

TABLE I-continued

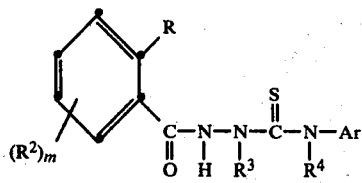

| Compound No. | R | m | R² | R³ | R⁴ | Ar | M.P. °C. |
|---|---|---|---|---|---|---|---|
| 3580 | (—COO)₃Fe | " | — | —CH₃ | —H | phenyl | 152–157° (dec.) |
| 3581 | (—COO)₂Mn | " | — | —CH₃ | —H | phenyl | 158–160° (dec.) |
| 3582 | (—COO)₂Fe | " | — | —CH₃ | —H | phenyl | 160–180° (dec.) |
| 3676 | —COOH | 2 | 4,5-dichloro | —H | —H | phenyl | 164° (dec.) |
| 3716 | —CH₂OH | 0 | — | —CH₃ | —H | 3-fluorophenyl | 136–137° |
| 3873 | —CONH—CH₂CH₂—phenyl | " | — | —CH₃ | H | phenyl | 154–156° |
| 3874 | —CONH—CH₂—4-fluorophenyl | " | — | —CH₃ | H | phenyl | 156–158° |
| 3875 | —CONH—benzyl | " | — | —CH₃ | H | phenyl | 143–146° |
| 3876 | —CONH—nonyl | " | — | —CH₃ | H | phenyl | 151–152° |
| 3877 | —CONH—CH₂—(4-methoxyphenyl) | " | — | —CH₃ | H | phenyl | 149–151° |
| 3879 | —CONH-cyclopropyl | " | — | —CH₃ | H | phenyl | 144–146° |
| 3880 | —CON(CH₂CH₂CH₃)₂ | " | — | —CH₃ | H | phenyl | 132–134° |
| 3883 | —CONH—CH₂CHCH₂—CH₂CH₂CH₃ (C₂H₅) | " | — | —CH₃ | H | phenyl | 143–145° |
| 3884 | —CONH(CH₂)₄CH₃ | " | — | —CH₃ | H | phenyl | 145–147° |
| 3866 | —CON—benzyl / isopropyl | " | — | —CH₃ | H | phenyl | 167–169° |
| 3869 | —CON—benzyl / ethyl | " | — | —CH₃ | H | phenyl | 132–134° |
| 3872 | —CONHC(CH₃)₃ | 2 | 3,6-dichloro | —CH₃ | H | phenyl | 173–174° |
| 3974 | —CONH(CH₂)₃O—(CH₂)₂OCH₃ | 0 | — | —CH₃ | H | phenyl | 140–142° |
| 3975 | —CONH(CH₂)₃O—CH₂CH(CH₃)₂ | " | — | —CH₃ | H | phenyl | 146–148° |

UTILITY OF THE COMPOUNDS

The term "plant growth regulating" and cognate terms are used herein to refer to changes in the normal sequential development of a plant to agricultural maturity. Examples of such changes include shortening or lengthening of the internode distance, increasing flowering or the set of fruit, reducing plant stature, increasing branching or tillering, inhibiting sprouting, inhibiting sucker growth, fruit thinning, defoliation, desiccation, delayed flowering, increased tolerance to cold, drought, and other stress, increased root growth, and delayed senescence. Many others will be apparent to those skilled in the art.

As will be evident from the foregoing types of plant growth regulation, the compounds of formula I are principally intended to alter the further growth of desirable plants. However, because of the variation among plant species, some herbicidal action has been noted. For example, at rates that provide desirable plant growth regulation of some species, numerous compounds of formula I exhibit a herbicidal effect on *Digitaria sanguinalis* (crabgrass). Also, many of the present compounds exhibit at the same time or sequentially on a given species a plurality of growth regulating effects, not all of which are desirable. However, the criterion of plant growth regulation is a non-lethal effect which is desirable in overall terms.

The present plant growth regulants can be utilized on a wide variety of plant species. The regulants are of special value to agriculturally important crops, such as the grains, the legumes, and the numerous vegetable and fruit crops. However, the present regulants can also be used on ornamentals, house plants, and other plants grown principally or solely for their decorative value.

The plant growth regulating effect of the compounds of formula I is exhibited upon application to plants in any of their parts or viable forms. Thus, application can be made to plant foliage, stems, flowers, fruit, roots, rhizomes, tubers, seeds, and the like. Application can also be made to soil, to exert a plant growth regulating effect on seeds sown therein or plants already growing therein.

The amount of compound to be employed is not critical so long as an effective plant growth regulating amount is used. Application rates of from 0.01 oz. to 10 pounds per acre are generally suitable, but will vary with the particular compound of formula I employed, the plant species and its stage of growth, the nature of the growth regulation sought, and other factors known to those skilled in the art. Lower rates can be employed with many of the compounds. For example, 1-(2-carbomethoxybenzoyl)-2-methyl-4-phenyl-3-thiosemicarbazide is advantageously employed on soybeans at rates of 1 lb. per acre and less; favorable growth regulating effects have been observed as low as ½ oz. per acre, and the optimal rate at present appears to be about 1 oz. per acre. On strawberry fields, application of 1-(2-carboxybenzoyl)-2-methyl-4-phenyl-3-thiosemicarbazide at a rate of 0.1 oz. per acre increased berry production by 2400 lbs. per acre. Treatment of a dormant crab apple tree in spring with a 1000 ppm formulation of 1-(2-carbomethoxybenzoyl)-2-methyl-4-phenyl-3-thiosemicarbazide (in 50:50 kerosene:crop oil) resulted in a delay in flowering, fewer blossoms, and enlargement of the leaves.

In the instance of application to seeds, preliminary tests on *Soja max* (soybeans), *Hordeum vulgare* (barley), *Triticum aestivum* (wheat), *Oryza sativa* (rice), *Setaria italica* (German millet), and *Brassica napus* (rape) suggest application rates of no more than about 1 percent by weight of the seed.

As illustrated below, a single application results in desirable plant growth regulation. However, multiple applications throughout the growing season can be used to obtain maximum plant growth regulation.

In one preferred embodiment, the compounds of formula I are employed on *Soja max*. When the compounds are applied to the foliage of *Soja max*, the change to more desirable modes of plant growth, including an increase in number of blooms and seed pods, has been observed to last for at least 18 days, usually stimulating increased pod set on about six nodes of the plant. The best practice is to use repeated foliar applications, every 15 to 20 days starting at the earliest blossoms to achieve maximum benefit by this method. If soil application (including application to the seed) is the chosen method, persistence of the growth regulating effect for over 30 days has been observed, including effective control of certain weeds. Depending upon the nature of the crop and the length of the growing season, a single application to the soil (or to the crop seed) at planting time may be sufficient, or will at least bring the greatest overall economic return for the expense involved.

In another preferred embodiment of the present invention, the compounds of formula I are employed on tomato plants to increase the set of fruit.

The results obtained on legumes and and tomatoes indicate that the compound possesses a unique combination of both cytokinin and auxin activity. More Chlorophyll A is present in the treated plants, as indicated by color change. More photosynthesis occurs, as indicated by increase in weight of treated plants, although the plants may be slightly shorter in stature. The stimulation of both leaf growth and fruit set at the same time is extraordinary.

Although productivity of *Soja max* is described herein in terms of increased "pod count," this effect is another example of enhanced "fruit set". In this term, "fruit" is used in its broad botanical meaning of the ripened ovary or ovaries of a seed-bearing plant, together with accessary parts.

The compounds of Formula I, especially those which exist as oils, can be employed alone; however, the compounds are generally employed in formulations comprising one or more of the compounds and an agriculturally acceptable adjuvant. The adjuvant can be any substance which aids in the utilization of the plant growth regulating activity of the compounds of Formula I. For example, the adjuvant can be a solvent, an inert diluent, a surface active agent, a substance for dispersing an active agent as an aerosol, or the like.

Suitable inert diluents include powdered chalk, the attapulgite clays, the kaolin clays, the montmorillonite clays, the diatomaceous earths and the silicates. Suitable surface active agents include the sulfonated lignins, the naphthalenesulfonates, the alkylbenzenesulfonates, the adducts of alkylphenols, fatty acids, fatty alcohols, and the like with ethylene and/or propylene oxide, and the like.

Wettable powder formulations are a preferred type of formulation, especially for those compounds of Formula I which exist as solids. Wettable powders comprise an intimate finely-divided mixture of the compound of Formula I, an inert carrier, and a surface active agent. The inert carrier and surface active agent can be any of those identified above. Wettable powders are typically added to water to constitute ultimate treating formulations.

Emulsifiable concentrates also constitute a suitable type of formulation of the compounds of Formula I. Such concentrates comprise a mixture of a compound of Formula I, a water-immiscible solvent, and an emulsifier. Suitable solvents include the aromatic and aliphatic hydrocarbons and derivatives, especially the xylenes, the various petroleum distillates, and oils from natural products, such as corn oil, soybean oil, and cottonseed oil. The emulsifier can be any one or more of the surface active agents exemplified above. An emulsifiable concentrate is especially adapted to be added to water to constitute an ultimate treating formulation.

Those compounds of Formula I which are relatively soluble in water can also be formulated as water soluble concentrates, either liquid or solid. Such formulations advantageously contain, in addition to the compound of Formula I, a surface active agent of the type listed above which facilitates solution of the active ingredient when added to water to form the ultimate treating formulation.

In general, formulations desirably contain from about 0.1 percent to about 95 percent of compound of Formula I and from about 0.1 to about 75 percent of surface active agent. As noted, the formulations typically serve as concentrates to be diluted to ultimate treating formulations. However, in certain specialized modes of application known to those skilled in the art, these same concentrated formulations can be employed directly as treating formulations. Attention is directed to the rotary atomizer type of low volume sprayer known as the Micron Herbi Sprayer.

The compositions which are intended for use in the form of aqueous dispersions or emulsions can also comprise a humectant, that is to say, an agent which will delay the dying of the composition in contact with the vegetation to which it has been applied. Suitable humectants include glycerol, diethylene glycol, solubilized lignins, such as calcium lignosulfonate, and the like. The compositions may contain other ingredients, for example, protective colloids such as gelatin, glue, casein, gums and polyvinyl alcohol; sodium polyphosphate; cellulose ethers, stabilizers and stickers, for example non-volatile oils.

As noted above, the compounds of Formula I sometimes exhibit a plurality of growth regulant effects, not all of which are desirable. For example, application of the compounds of Formula I sometimes results in an initial negative effect, typically stunting, which is outgrown by the plants; and the plants at their agricultural maturity have achieved a net positive growth regulating effect. It has further been observed that the initial negative side effect can be minimized by the coapplication of a source of potassium ion, typically a potassium salt such as potassium dihydrogen phosphate.

The utility of the compounds of Formula I as plant growth regulants is illustrated by the following Examples.

EXAMPLE 13

A water soluble formulation of the active ingredient in salt form was prepared by combining 120 g of 1-(2-carboxybenzoyl)-2-methyl-4-phenyl-3-thiosemicarbazide, 400 ml of water and 173 g of polyoxyethylene (5) soyaamine (Ethomeen S-15). The mixture was stirred at ambient temperature for 10 hours at which time a clear solution was obtained. With stirring 200 g of trimethylnonyl polyethylene glycol ether (Tergitol TMN-10) was added. An additional 107 ml of water was added, resulting in a formulation having the following percentage weight composition:

| Active Ingredient | 12.0% |
|---|---|
| Polyoxyethylene (5) soyaamine | 17.3% |
| Trimethylnonyl polyethylene glycol ether | 20.0% |
| Water | 50.7% |

A sample of the above formulation was subjected to shelf-life studies. The solution was stable when stored at 15°–20° C.

EXAMPLE 14

A water soluble powder was prepared as follows: 60 g of potassium dihydrogen phosphate was ground in a shear-type blender and dried overnight in an oven at 50° C. The potassium dihydrogen phosphate was combined with 7 g of the potassium salt of 1-(2-carboxybenzoyl)-2-methyl-4-phenyl-3-thiosemicarbazide, 5 g of sodium naphthalene formaldehyde condensate (Morwet D-425) and 28 g of Atwet W-13 (a commercially prepared product containing 50% polyethoxylated fatty acid esters encapsulated within an equal weight of a water soluble organic material). All components were well blended. This water soluble formulation contained the following weight percentage:

| Active Ingredient | 7% |
|---|---|
| Potassium dihydrogen phosphate | 60% |
| Sodium naphthalene formaldehyde condensate (dispersant) | 5% |
| Atwet W-13 (50% nonionic encapsulated surfactant) | 28% |

EXAMPLE 15

By shearing and blending procedures, a water soluble formulation of the following weight percentage was prepared:

| Ammonium salt of 1-(2-carboxybenzoyl)-2-methyl-4-phenyl-3-thiosemicarbazide | 25% |
|---|---|
| Sodium naphthalene formaldehyde condensate (dispersant) | 5% |
| Atwet W-13 (50% nonionic encapsulated surfactant) | 70% |

The formulation was a white powder mixture. The pH of a one percent aqueous solution of the mixture was 5.93. The bulk density of the formulation was 22 lbs/ft$^3$.

EXAMPLE 16

A wettable powder formulation of increased active ingredient content was prepared by thoroughly blending 150 g of 1-(2-carboxybenzoyl)-2-methyl-4-phenyl-3-thiosemicarbazide, 30 g of Georgia attapulgite clay, 10 g of sodium diisopropyl naphthalene sulfonate (Morwet IP) and 10 g of sodium naphthalene formaldehyde condensate (Morwet D-425). The mixture was ground in an air mill. The average particle size was determined to be about 5 microns. The resulting formulation had the following percentage weight composition:

| Active Ingredient | 75% |
|---|---|
| Georgia attapulgite clay | 15% |
| Sodium diisopropyl naphthalene sulfonate (wetting agent) | 5% |
| Sodium naphthalene formaldehyde condensate (dispersant) | 5% |

EXAMPLE 17

A suitable wettable powder formulation was obtained by blending and milling 0.72 lb of precipitated silica (Hi-Sil 233), 0.80 lb of trimethylnonyl polyethylene glycol ether (Tergitol TMN-10), 0.40 lb 1-(2-carbomethoxybenzoyl)-2-methyl-4-phenyl-3-thiosemicarbazide and 0.08 lb of sodium naphthalene formaldehyde condensate (Morwet D-425) as a dispersing agent. The resulting formulation had the following percentage weight composition:

| Active ingredient | 20% |
|---|---|
| Precipitated silica | 36% |
| Trimethylnonyl polyethylene glycol ether | 40% |
| Sodium naphthalene formaldehyde condensate | 4% |

The above composition had a bulk density of 15.3 lbs/ft$^3$, an average particle size of 10.4 microns and a wetting time of 49 seconds.

EXAMPLE 18

A water dispersion of the present active agent was prepared by mixing 0.06 lb of 1-(2-carbomethoxybenzoyl)-2-methyl-4-phenyl-3-thiosemicarbazide, 0.12 lb of sorbitan monooleate ethoxylate (Tween 80) and 0.82 lb of tetrahydrofurfuryl alcohol. When diluted with water for spraying, the formulation produced microcrystals of the active ingredient, suspended uniformly by the surface active agent.

EXAMPLE 19

An emulsifiable concentrate suitable for implementing the plant growth regulant activity of the compounds of Formula I is prepared by dissolving the active ingredient and a wetting agent in an oil from a natural product or in an aromatic hydrocarbon solvent. A typical emulsifiable concentrate given in percentage weights is:

| | |
|---|---|
| 1-(2-((2-ethylhexyloxy)carbonyl)-benzoyl)-2-methyl-4-phenyl-3-thiosemicarbazide | 12% |
| Dialkylphenoxypolyethoxylated ethanol (Igepal DM-530) | 12% |
| Corn oil | 76% |

EXAMPLE 20

A water soluble powder suitable for implementing the plant growth regulant activity of the compounds of Formula I is prepared by blending the active ingredient in salt form with a solid anionic surfactant such as Naxonate KX (potassium xylene sulfonate) or Naxonate KT (potassium toluene sulfonate). If further dilution is required, a compatible inorganic salt may be included. An illustrative water soluble powder has the following percentage weight composition:

| | |
|---|---|
| Potassium salt of 1-(2-carboxybenzoyl)-2-methyl-4-phenyl-3-thiosemicarbazide | 6.2% |
| Potassium carbonate | 50.0% |
| Naxonate KX (potassium xylene sulfonate) | 43.8% |

Solid nonionic surfactants such as Myrj 53 (polyoxyethylene (50) stearate) can also be used.

EXAMPLE 21

Another water soluble powder is prepared by conventional procedures to have the following percentage weight composition:

| | |
|---|---|
| Potassium salt of 1-(2-carboxybenzoyl)-2-methyl-4-phenyl-3-thiosemicarbazide | 6.2% |
| Morwet D-425 (sodium naphthalene formaldehyde condensate) | 5.0% |
| Macol SA-40 (polyoxyethylene (4) Lauryl alcohol) | 44.4% |
| Sorbitol | 44.4% |

EXAMPLE 22

A further emulsifiable concentrate formulation is prepared with the active ingredient in salt form, by mixing the following reagents given as weight percentage:

| | |
|---|---|
| 1-(2-carboxybenzoyl)-2-methyl-4-phenyl-3-thiosemicarbazide | 4.5% |
| 2,6-lutidine | 1.5% |
| Atlox 3459F (anionic-nonionic blend of calcium dodecylbenzene sulfonate and polyethoxylated fatty acid esters) | 10.0% |
| Cyclohexanone | 84% |

EXAMPLE 23

The use of the growth regulant compounds to modify and control plant growth as well as to combat unwanted vegetation may be demonstrated readily in small scale greenhouse tests according to procedures described below.

PRE-EMERGENT APPLICATION

Disposable plastic trays about 2½ inches deep were filled with soil and sprayed with aqueous spray mixtures at a rate of 5 lb of active chemical per acre of sprayed area, were seeded with 6 species of plant seeds and then covered with about 1/4 inch of soil. The spray mixtures were prepared by dissolving the proper amount of growth regulant compound in 15 ml of acetone, adding 4 ml of a solvent-emulsifier mixture consisting of 60 wt. percent of a commercial polyethoxylated vegetable oil emulsifier (96 wt. percent active ingredient, Emulphor EL-719), 20 wt. percent xylene and 20 wt. percent deodorized kerosene, then bringing total volume up to 60 ml by addition of warm water. Twenty-one days after seeding and treatment the plantings were examined and effects were rated according to the following schedule.

| Effect | Abbreviation in Tables |
|---|---|
| Formative effect on new growth | F |
| Epinasty | E |
| Growth reduction | G |
| Necrosis | N |
| Non-emergence | K |

| Degree of Effect |
|---|
| 0 = no effect |
| 1 = slight effect, temporary |
| 2 = moderate effect |
| 3 = severe effect |
| 4 = maximum effect |

In some instances more than one effect was observed and recorded with respect to a group of plants of one species.

POST-EMERGENT APPLICATION

Several species of plants were grown in potting soil in disposable polystyrene foam trays and individual plants of a miniature variety of *Lycopersicum esculentum* were grown in four-inch pots in the greenhouse. Aqueous spray formulations were prepared and the growing plants were sprayed at a spray volume of 60 gallons per acre and an application rate of 5 lb per acre. Spray mixtures were prepared in the manner described above.

For comparative purposes, plants were also sprayed at 60 gal. per acre with a spray mixture containing no growth regulant. Effects were again rated according to the schedule disclosed above.

Observations of effects in both pre- and post-emergent tests were recorded, and are tabulated in Table I, below:

| | EFFECTS ON VEGETATION | | | | | | | | | | | |
|---|---|---|---|---|---|---|---|---|---|---|---|---|
| | Pre-Emergent Effects | | | | | | Post-Emergent Effects | | | | | |
| Compd. No. | *Digitaria sanguinalis* | *Celosia plumosa* | *Bromus inermis* | *Setaria italica* | *Raphanus sativus* | *Beta vulgaris* | *Setaria italica* | *Medicago sativa* | *Avena sativa* | *Raphanus sativus* | *Beta vulgaris* | *Lycopersicum esculentum* |
| 597 | K4 | F2G1 | K3G3 | F3G3 | F3G2 | F3G2 | N1G1 | F3 | F2 | G1F1 | F2G1 | F3 |
| 1685 | K4 | F3G3 | F3G3 | F3G3 | F1G1 | F3G3 | 0 | 0 | 0 | 0 | F2 | N1F1 |
| 1686 | 0 | F1 | F2 | 0 | 0 | F2 | C1 | F1 | 0 | N1 | F2G1 | N1F1 |
| 2005 | K4 | F3G2 | K4 | F3G3 | G3 | K4 | 0 | F2G1 | G1 | G2F1 | F3G1 | F2 |
| 2008 | 0 | K2 | F1 | 0 | K2 | K1 | 0 | F2G2 | N1G1 | F2G1 | F2G1 | 0 |
| 2044 | K4 | F1G1 | F3G3 | F2G2 | F1G2 | K4 | F2G1 | F3G1 | F2 | N1G1 | F2G1 | F2G3 |
| 2047 | F3G2 | F1 | F2G1 | F2G1 | F1 | F2 | F2G1 | F2G2 | F1G1 | F2G1 | F2G2 | F2G2 |
| 2322 | N1 | N3G2 | G1 | 0 | 0 | N3G3 | 0 | 0 | 0 | 0 | F1 | 0 |
| 2324 | K1G2 | 0 | 0 | 0 | 0 | K1 | 0 | 0 | 0 | 0 | F1 | 0 |
| 2325 | N3G3 | N3G2 | N3G3 | N2G3 | G3 | K3G2 | N1F1 | F2 | F1 | F1G1 | F1G1 | F33 |
| 2341 | F2G1 | F1 | F2 | F3G2 | G1 | F2G1 | F1 | F1 | 0 | F1G1 | F1G1 | 0 |
| 2342 | F1 | 0 | F2 | F2 | 0 | F2 | 0 | F1 | 0 | F2G1 | F1G2 | F1 |
| 2370 | K4 | K4 | K4 | F3G3 | F3G2 | F3G3 | F2G1 | N1G3 | N1G1 | N1F1 | F1G3 | F3 |
| 2371 | K4 | K4 | F3G3 | F3G3 | F3G3 | F3G3 | N1G1 | F3G3 | F1G1 | F2G2 | F1G2 | F3G3 |
| 2372 | K4 | F3G3 | F3G3 | F3G3 | F3G3 | F3G2 | N1G2 | N1G3 | N1 | N1G2 | F3G2 | F3 |
| 2388 | F2G2 | F1G1 | F3G1 | F3G2 | F3G2 | F3G1 | 0 | F3G1 | F1 | F2 | F3G1 | F3 |
| 2389 | K4 | K4 | K3F1 | F3G3 | F3G3 | K4 | F2 | F3G3 | F2 | F2 | F3G3 | F3 |
| 2390 | K3G3 | F3G2 | F3G1 | F3G3 | F3G2 | F3G2 | F1 | F3G2 | F1 | F1 | F2G1 | F3 |
| 2391 | K4 | K4 | K3F1 | F3G3 | F3G3 | F3G3 | F2 | F3G2 | F2G2 | F1 | F3G1 | F3 |
| 2392 | F3G3 | F3G3 | F3G1 | F3G2 | F2G1 | F3G1 | 0 | F1 | 0 | 0 | F2 | F2 |
| 2414 | K4 | F3G3 | F3G3 | F3G3 | F3G3 | F3G3 | F2 | F3G3 | F2 | F1 | F3G1 | F3 |
| 2415 | K4 | F3G3 | K4 | F3G3 | F3G2 | F3G3 | F2 | F3G3 | F1 | 0 | F3G1 | F3 |
| 2418 | F1G1 | K2 | F2G1 | 0 | 0 | F2G1 | 0 | F1 | 0 | 0 | F2 | F2 |
| 2422 | 0 | 0 | F2 | 0 | 0 | 0 | — | — | — | — | — | — |
| 2432 | K4 | F3G3 | F3G3 | F3G3 | F3G3 | F3G3 | F2 | F3G2 | F1 | F2 | F3G1 | F2 |
| 2433 | F3G2 | F3G3 | F2G1 | F2G1 | F3G2 | F1G1 | F1 | F3G2 | F1 | F1 | F3G2 | F3 |
| 2434 | F3G3 | F3G3 | F3G1 | F2G1 | F3G1 | F1 | F1 | F3G2 | F2 | F1 | F2G1 | F3 |
| 2444 | K4 | K2G1 | F3G1 | F3G2 | F1G2 | F2G2 | N2G2 | — | — | F2 | N2G1 | F3 |
| 2445 | F3G3 | K2G1 | F3G1 | F3G2 | F1G1 | F2G2 | 0 | F2 | 0 | 0 | F2G1 | F2 |
| 2446 | K4 | K4 | F3G3 | F3G3 | F2G2 | F3G2 | — | F2G1 | 0 | F1 | F1G2 | F1 |
| 2450 | F2G2 | K4 | F2 | F3G2 | F2G2 | F3G2 | N1G1 | F2G1 | 0 | F1 | F2 | F1 |
| 2470 | K4 | K4 | F3G3 | F3G3 | F3G2 | 0 | N1 | F2 | 0 | F1 | F2G2 | F2G2 |
| 2472 | F3G3 | K4 | F3G2 | F3G3 | F1G1 | F2G2 | 0 | F2G1 | 0 | N1F1 | F2G1 | F3G2 |
| 2474 | K4 | K4 | F3G3 | F3G3 | F3G2 | F3G2 | N1 | N1G2 | 0 | N1G1 | F2G2 | F3 |
| 2479 | 0 | 0 | F1 | F1 | 0 | 0 | N1G2 | F1 | N1 | F1 | F1G1 | 0 |
| 2480 | 0 | 0 | 0 | 0 | 0 | 0 | — | — | — | — | — | — |
| 2481 | K4 | K4 | F3G3 | F3G3 | F3G2 | F3G2 | N1G2 | N3G3 | G1 | F2G1 | N4 | F2G1 |
| 2482 | K4 | K4 | F3G3 | F3G3 | F3G2 | K4 | N1G2 | F2G1 | F1G1 | F2G1 | F2G2 | F2G1 |
| 2483 | F3G3 | K4 | F3G3 | F3G2 | F3G2 | F3G2 | N3G3 | F2G3 | G1 | F2G1 | F2G1 | F3 |
| 2484 | F3G2 | F3G3 | F3G2 | F3G1 | F2G1 | F3G2 | N2G1 | F1 | G1 | F1G1 | F2G2 | F1 |
| 2487 | K4 | F3G2 | F3G3 | F3G3 | F3G3 | F3G3 | N1G1 | — | N1 | F2G2 | F2G1 | F2 |
| 2488 | F3G3 | F3G2 | F3G3 | F3G3 | F3G2 | F3G2 | N1G2 | F2G2 | F1G1 | N1F1 | F2G1 | F3G2 |
| 2563 | F2G2 | G2G1 | F3G1 | F3G2 | F2G1 | F2G1 | N3G3 | F1 | 0 | 0 | F2G1 | F3E2 |
| 2564 | F1G1 | F1G1 | F3G1 | F3G2 | F1G1 | F1G1 | N1G1 | 0 | 0 | 0 | F1 | F3E2 |
| 2567 | K4 | F3G2 | F3G3 | F3G3 | F3G2 | F3G3 | N4 | F3G2 | F1 | F2 | F3G2 | F3G3 |
| 2568 | F3G3 | F3G3 | F3G3 | F3G3 | F3G2 | F3G3 | N1G2 | F3G2 | F2 | F2 | F3G1 | F3E3 |
| 2569 | K4 | F3G3 | F3G3 | F3G3 | F3G3 | F3G3 | F2G2 | F3G2 | F1 | F2G1 | F3G2 | F3G2 |
| 2570 | F3G3 | F3G3 | F3G2 | F3G2 | F3G3 | F3G3 | F2G2 | F3G2 | F1 | F2 | F3G2 | F3G2 |
| 2571 | F2G2 | F2G1 | F3G1 | F3G2 | F2G1 | F1G1 | F1G1 | F2 | 0 | F1 | F2 | F3E2 |
| 2572 | F2G1 | F2G1 | F1 | F2G1 | F1G1 | F1 | F1 | F2 | 0 | F2G1 | F3G2 | F3G2 |
| 2573 | F1 | F1 | F2 | F1 | 0 | 0 | 0 | F1 | 0 | 0 | F1 | F1 |
| 2574 | F1 | F1 | F2 | 0 | 0 | 0 | 0 | F1 | 0 | 0 | F2 | F1 |
| 2476 | 0 | 0 | 0 | 0 | 0 | 0 | — | — | — | — | — | — |
| 2577 | F1G1 | F1G1 | F2 | F2G1 | F1 | F1 | N1 | F1 | 0 | 0 | F2 | 0 |
| 2578 | F1 | F1 | F2 | F1 | 0 | 0 | 0 | F1 | 0 | 0 | F2 | F1 |
| 2579 | K4 | F3G3 | F3G3 | F3G3 | F3G2 | F3G1 | F2G1 | F3G3 | F1 | F2G1 | F3G2 | F3E2 |
| 2580 | 0 | 0 | F1 | 0 | 0 | 0 | 0 | F1 | 0 | F1 | F2 | 0 |
| 2581 | F2G1 | 0 | F1 | 0 | 0 | 0 | 0 | F1 | 0 | 0 | F1 | 0 |
| 2583 | F1G1 | F1 | F2 | F1 | 0 | F1 | 0 | F3G1 | F1 | F1 | F3G1 | F1 |
| 2584 | F1 | F1 | F2 | F1 | 0 | 0 | 0 | F3G1 | F1 | F1G1 | F2G1 | F1E1 |
| 2585 | F3G3 | F3G2 | F3G3 | F3G3 | F1 | F3G1 | F1 | F3E2 | F1 | F1G1 | F3G1 | F3E2 |
| 2586 | F1 | F1 | F2 | F1 | 0 | 0 | 0 | F3G2 | 0 | F2G1 | F3G1 | F1E1 |
| 2588 | F1 | 0 | F1 | 0 | 0 | 0 | 0 | 0 | 0 | F1 | F1 | 0 |
| 2589 | 0 | 0 | 0 | 0 | 0 | 0 | 0 | F1 | 0 | 0 | F1 | 0 |
| 2590 | 0 | 0 | F1 | F1 | 0 | 0 | F1 | F3G2 | F1 | F2 | F3G1 | F1E1 |
| 2591 | K4 | K3G3 | K3G2 | F3G3 | F3G2 | F3G1 | F3G3 | F3G3 | F1G1 | F3G1 | F3G3 | F3G3 |
| 2592 | F3G3 | F3G3 | F3G3 | F3G3 | F3G2 | F2G1 | F3G2 | F3G1 | F1 | F2G1 | F2G1 | F3G3 |
| 2594 | F3G3 | F3G2 | K4 | F3G3 | N4 | F2G1 | N4 | F3G3 | G1 | F2G1 | F3G1 | F3G1 |
| 2595 | F2G2 | F1G1 | F3G1 | F2G1 | G1 | F2G1 | N1G3 | F3G3 | F1G1 | F1G1 | F3G2 | F3E3 |
| 2597 | F1G1 | F2G1 | F3 | F2G1 | F1G1 | F2G1 | G3F2 | F3G2 | F1 | F2G1 | F3G2 | F3G3 |
| 2598 | 0 | 0 | F1 | 0 | 0 | 0 | F1G1 | F3G1 | F1 | F2G1 | F3G1 | F2E2 |
| 2599 | F1 | F2 | F2 | 0 | 0 | 0 | 0 | F3G1 | 0 | F1 | F2 | F2E1 |

-continued

| | EFFECTS ON VEGETATION | | | | | | | | | | | |
|---|---|---|---|---|---|---|---|---|---|---|---|
| | Pre-Emergent Effects | | | | | | Post-Emergent Effects | | | | | |
| Compd. No. | Digitaria sanguinalis | Celosia plumosa | Bromus inermis | Setaria italica | Raphanus sativus | Beta vulgaris | Setaria italica | Medicago sativa | Avena sativa | Raphanus sativus | Beta vulgaris | Lycopersicum esculentum |
| 2603 | 0 | 0 | 0 | 0 | 0 | 0 | 0 | F1 | 0 | F1G1 | 0 | F1E1 |
| 2604 | F2 | F1G1 | F3G1 | F3G2 | 0 | F1 | 0 | F2 | F1 | F2G1 | F2G1 | F2E2 |
| 2605 | F3G1 | F2G1 | F2 | F1G1 | 0 | 0 | F2G1 | F2 | 0 | F2G1 | F2G1 | F2E1 |
| 2622 | F3G2 | F3G2 | K4 | F3G3 | F3G2 | F3G2 | N3G3 | F3G2 | F1 | F2G1 | F3G2 | F3E3 |
| 2627 | K4 | F3G3 | F3G3 | F3G3 | F3G2 | F3G3 | F2G2 | F3G2 | F1G1 | F3G3 | F3G3 | F3E3 |
| 2628 | F3G3 | F2G1 | F3G3 | F3G3 | F3G2 | F3G3 | F2G2 | F3G2 | F1 | F1G1 | F3G2 | F3E3 |
| 2633 | K4 | F3G3 | K4 | F3G3 | F3G2 | F3G3 | F3G3 | F3G2 | F2G1 | F2G1 | F3G2 | F3E3 |
| 2634 | F3G3 | F3G2 | F3G3 | F3G3 | F3G2 | F3G3 | F1G1 | F3G2 | F1 | F1 | F2 | F3E2 |
| 2635 | F3G2 | F3G2 | F3G3 | F2G2 | F3G2 | F1G1 | F3G2 | F1 | F1G1 | F2G1 | F3E3 | |
| 2636 | F3G3 | F3G2 | F3G3 | F2G2 | F2G2 | F2G3 | F3G2 | F1 | F1G1 | F3G2 | F3E3 | |
| 2637 | K4 | F3G2 | K4 | F3G3 | F3G2 | F3G3 | F3G3 | F3G3 | F1G1 | F2G1 | F3G2 | F3E3 |
| 2641 | F2G1 | F2G2 | F2G1 | F3G2 | F1G1 | F2G1 | F3G3 | F3G3 | F1 | F1G1 | F3G2 | F3G1 |
| 2668 | K4 | F3G3 | K4 | F3G3 | F3G1 | F3G3 | G2F2 | F3G2 | F1G1 | F2G1 | F3G3 | F3G3 |
| 2669 | F3G3 | F3G2 | K4 | F3G3 | F3G2 | F3G3 | F2G2 | F3G2 | F2G1 | F2G1 | F3G2 | F3E3 |
| 2697 | F2G3 | F1G1 | F3G1 | F2G1 | F1 | F1G1 | F2G1 | F3G3 | F2G1 | F3G1 | F3G1 | F3E2 |
| 2698 | F1 | 0 | 0 | 0 | 0 | 0 | F1 | F1 | F1 | F1G1 | F2G1 | F1 |
| 2699 | F1 | F1G1 | F1 | 0 | 0 | 0 | F1 | F1G1 | 0 | F2G1 | F2G1 | F3E1 |
| 2700 | 0 | 0 | 0 | 0 | 0 | 0 | F1 | F1 | 0 | F1 | F2 | F3E1 |
| 2701 | F1G1 | F1G1 | F3G1 | F1 | G1 | 0 | F2G1 | F3G2 | F1 | F2G1 | F3G1 | F3E2 |
| 2702 | F3G1 | F1 | F3 | F3G1 | F1 | F2G1 | F2G1 | F3G2 | 0 | F2G1 | F3G1 | F2 |
| 2704 | F2G1 | F1G1 | F3G1 | F1G1 | 0 | F1 | F1 | F3G1 | F1 | F3G1 | F2G1 | F3E1 |
| 2705 | F1 | F1G1 | F2 | F1 | 0 | F1 | F2G1 | F3G2 | F2 | F2G1 | F3G1 | F2 |
| 2707 | F1 | 0 | 0 | 0 | 0 | 0 | F1 | F2 | F1 | F2G2 | F3G1 | F1 |
| 2708 | 0 | 0 | 0 | 0 | 0 | 0 | F1 | F1 | 0 | F1 | F2 | F2E1 |
| 2721 | F3G3 | F2G2 | F3G2 | F3G2 | F3G2 | F3G3 | F2G2 | F3G3 | F2G1 | F3G1 | F3G2 | F3G3 |
| 2722 | K4 | F2G2 | F3G3 | F3G2 | F3G3 | F3G3 | F2G1 | F3G2 | F1 | F3G1 | F3G1 | F3E3 |
| 2723 | F3G3 | F2G2 | F3G2 | F3G2 | F3G2 | F3G2 | F2G1 | F2 | F1 | 0 | F3 | F3E2 |
| 2724 | K4 | F3G3 | K4 | F3G3 | F3G3 | K4 | F2G2 | F3G2 | F1G1 | F2G1 | F3G2 | F3E3 |
| 2725 | F3G2 | F2G1 | F3G1 | F3G1 | F1G1 | F2G2 | F1 | F3G1 | 0 | F2 | F3G1 | F3E2 |
| 2726 | F3G2 | F1 | F2 | F2G1 | F1G1 | F2G1 | F1 | F3G1 | F1 | F1 | F2 | F2E1 |
| 2727 | F1G1 | F1 | F2 | F2G1 | 0 | 0 | F1 | F2G1 | 0 | F1 | F2 | F2 |
| 2728 | F3G2 | F2G2 | F3G1 | F3G1 | F1G1 | F1G1 | F1G1 | F3G3 | F2G1 | F2G1 | F2G1 | F3E1 |
| 2729 | F1G1 | F2G2 | F1 | 0 | 0 | 0 | F1 | F2 | 0 | 0 | F1 | F1 |
| 2732 | F1 | 0 | F1 | F1G1 | 0 | 0 | 0 | F1 | 0 | 0 | F1 | F1 |
| 2733 | F3G2 | N4 | F2 | F3G2 | F1 | F1 | 0 | F1 | 0 | 0 | F1 | 0 |
| 2734 | F3G3 | F2G2 | F3G3 | F3G3 | F3G2 | F3G2 | F2G2 | F3G2 | F2 | F2G1 | F3G1 | F3E3 |
| 2735 | F3G3 | N4 | F3G3 | F3G3 | F3G2 | F3G2 | F2G2 | F2G1 | F2G1 | F2G1 | F3G1 | F3E3 |
| 2736 | F3G3 | F3G2 | F3G2 | F3G3 | F3G2 | F3G2 | F2G2 | F3G1 | F1 | F2G1 | F3G2 | F3G3 |
| 2740 | K4 | F3G2 | K4 | F3G3 | F3G3 | N4 | F2G2 | F3G2 | F2G1 | F2G1 | F3G1 | F3G3 |
| 2741 | F3G3 | F3G2 | F3G3 | F3G3 | F3G2 | K4 | F2G2 | F3G1 | F1 | F2G1 | F3G1 | F3E2 |
| 2742 | K4 | N4 | F3G3 | F3G3 | F3G2 | F3G3 | F2G2 | F3G2 | F2G1 | F2G1 | F3G2 | F3G3 |
| 2743 | K4 | F3G2 | F3G3 | F3G2 | F2G1 | F2G1 | F2G2 | F3G2 | F2G1 | F2G1 | F3G1 | F3E2 |
| 2744 | F3G3 | F3G2 | F3G3 | F3G3 | F3G2 | F3G2 | F1G1 | F3G2 | F1G1 | F1 | F3G1 | F3E2 |
| 2745 | F3G3 | K4 | F3G3 | F3G2 | F2G2 | F2G2 | F3G1 | F1G1 | F1 | F3G2 | E2F2 | |
| 2746 | F2G1 | F2G2 | F3G1 | F3G3 | F2G1 | F2G1 | 0 | F1 | 0 | F1 | F2 | F1 |
| 2749 | 0 | 0 | 0 | 0 | 0 | 0 | 0 | 0 | 0 | 0 | F1 | 0 |
| 2750 | 0 | 0 | F1 | 0 | 0 | 0 | 0 | F1 | 0 | 0 | F1G1 | F1 |
| 2753 | K2 | G1 | F1 | 0 | 0 | G1 | 0 | 0 | 0 | 0 | F1 | 0 |
| 2754 | 0 | 0 | 0 | 0 | 0 | 0 | 0 | F1 | 0 | 0 | F1 | 0 |
| 2756 | F1G1 | F1 | F1 | F3G2 | F1 | F2G2 | F1 | F3 | 0 | F1 | F2G1 | F2E1 |
| 2760 | 0 | G1 | 0 | 0 | 0 | F1G1 | 0 | F1 | 0 | 0 | F1 | F1 |
| 2762 | 0 | 0 | 0 | 0 | 0 | 0 | 0 | F1 | 0 | 0 | F1 | 0 |
| 2771 | K4 | F3G2 | F3G3 | F3G3 | F3G2 | F2G2 | F3G3 | F3G2 | F1G1 | F1 | F3G2 | F3G3 |
| 2772 | F1 | F1 | F2 | F1G1 | F1 | F1G1 | 0 | F1 | 0 | 0 | F1 | F1E1 |
| 2777 | F1 | G1 | F2 | F1G1 | F1 | F1 | F1 | F1 | 0 | 0 | F2G1 | F1 |
| 2778 | 0 | 0 | F1 | 0 | G1 | 0 | 0 | F1 | 0 | F1 | F2 | F1 |
| 2779 | 0 | 0 | F1 | 0 | 0 | 0 | 0 | F1 | 0 | 0 | F1 | 0 |
| 2781 | 0 | 0 | F1 | 0 | 0 | 0 | F1 | F2 | 0 | 0 | F2 | 0 |
| 2783 | F1 | 0 | F1 | F1G1 | F1 | 0 | G1 | F2 | 0 | F2G1 | F2G1 | F1 |
| 2784 | F3G2 | F3G2 | F3G1 | F3G3 | F3G3 | F3G2 | F3G3 | F3G3 | F1G1 | F2G1 | F3G2 | F3E3 |
| 2787 | F1 | F1 | F2 | F2G1 | F1 | F1 | F1 | F1 | 0 | F1 | F2 | F1E1 |
| 2788 | F3G3 | F2G2 | F3G3 | F3G3 | F3G3 | F3G2 | F3G2 | F3G2 | F1G1 | F1 | F3G2 | F3E3 |
| 2790 | K4 | F3G2 | F3G3 | F3G3 | F3G2 | F3G3 | F3G2 | F3G2 | F2G2 | F2 | F3G1 | F3E3 |
| 2795 | F2G2 | F1G1 | F2 | F3G2 | F2G1 | F1G1 | F1 | F2 | F1 | 0 | F2G2 | F1 |
| 2796 | F1 | 0 | F2 | F3G2 | F1G1 | F1G1 | 0 | F1 | 0 | 0 | F2 | F1 |
| 2798 | 0 | 0 | 0 | 0 | 0 | F1 | 0 | F3 | 0 | F1G1 | F2G2 | F3E2 |
| 2799 | F1G1 | F1 | F2G1 | F1G1 | 0 | F1G1 | F1G1 | F3G1 | F1 | G1 | F2G1 | F2E1 |
| 2800 | 0 | 0 | 0 | 0 | 0 | 0 | F1 | F2 | 0 | F1G1 | F2G1 | F1 |
| 2801 | 0 | G1 | F1 | 0 | F1 | F1 | 0 | 0 | 0 | 0 | F1 | 0 |
| 2802 | F2G2 | F1 | F2G1 | F3G2 | F2 | F2G1 | F1 | F3G2 | 0 | F1 | F2G1 | F3E2 |
| 2803 | F3G3 | F2G1 | F3G3 | F3G3 | F3G2 | F3G1 | F1 | F3G2 | 0 | F1 | F3G1 | F3E3 |
| 2818 | F2G2 | F2G1 | F2 | F3G3 | F2G2 | F2G2 | F1G1 | F2G1 | F1 | 0 | F3G1 | F2E2 |
| 2819 | 0 | 0 | 0 | G1 | 0 | F1 | 0 | F2 | 0 | F1 | F2 | F2 |
| 2822 | K4 | F3G2 | F3G3 | F3G3 | F3G3 | F3G3 | F2G2 | F3G2 | F1G1 | F1 | F3G2 | F3E3 |
| 2844 | F2G3 | F3G2 | F3G3 | F3G3 | F2G2 | F2G2 | F3G2 | N1G3 | F1G2 | F2G2 | F3G2 | F3G3 |
| 2845 | K4 | F3G3 | F3G3 | F3G3 | F3G2 | F3G2 | N2G2 | F3G3 | 0 | N1G2 | F2G3 | F3G1 |
| 2850 | 0 | 0 | 0 | 0 | 0 | 0 | — | — | — | — | — | — |

-continued

| | Pre-Emergent Effects | | | | | | Post-Emergent Effects | | | | | |
|---|---|---|---|---|---|---|---|---|---|---|---|---|
| Compd. No. | Digitaria sanguinalis | Celosia plumosa | Bromus inermis | Setaria italica | Raphanus sativus | Beta vulgaris | Setaria italica | Medicago sativa | Avena sativa | Raphanus sativus | Beta vulgaris | Lycopersicum esculentum |
| 2851 | 0 | 0 | 0 | 0 | 0 | 0 | 0 | N2 | 0 | N1G1 | F2 | 0 |
| 2852 | 0 | 0 | 0 | 0 | 0 | 0 | 0 | 0 | 0 | 0 | F1G1 | 0 |
| 2853 | F2G1 | F1G1 | F3 | F3G1 | F1G1 | F2G1 | 0 | 0 | 0 | 0 | F1 | 0 |
| 2854 | K4 | K3G3 | F3G3 | F3G3 | F2G2 | F3G3 | N2G1 | F2G1 | N1G1 | N1F1 | F2G2 | F3 |
| 2855 | F3G3 | F3G2 | F3G2 | F3G2 | F1G1 | F2G2 | N1 | F2 | N1 | N1G1 | F2G1 | F2 |
| 2859 | K4 | K4 | F3G2 | F3G3 | F3G2 | K4 | N2G2 | F3G1 | 0 | 0 | F2G2 | N1F2 |
| 2862 | F1 | 0 | F1 | F1 | 0 | 0 | N1G1 | 0 | 0 | 0 | F2G1 | F2 |
| 2863 | F1 | 0 | 0 | 0 | 0 | 0 | 0 | F1 | 0 | 0 | F2 | 0 |
| 2879 | F3G3 | F1G1 | F3G2 | F3G2 | F2G2 | F3G3 | N2G1 | 0 | 0 | F2G1 | F2G3 | |
| 2882 | K4 | F3G2 | F3G3 | F3G3 | F3G2 | F3G3 | N1G2 | F2G2 | F2 | F1 | F2G2 | F3 |
| 2883 | K4 | F3G3 | F3G3 | F3G3 | F3G3 | K4 | N2G2 | F2G1 | N1 | N1G1 | F1G1 | F2 |
| 2885 | F3G3 | F2G2 | F3G2 | F3G2 | F3G2 | F3G3 | N3G2 | F2G1 | N1G1 | G1F1 | F1G2 | F2 |
| 2896 | F3G3 | F1G1 | F3G2 | F3G2 | F2G2 | F2G2 | N2G3 | 0 | N1 | 0 | F2G2 | F3G3 |
| 2898 | 0 | 0 | F1 | 0 | 0 | 0 | 0 | 0 | 0 | F1 | F2G1 | F1 |
| 2914 | 0 | 0 | 0 | 0 | 0 | 0 | 0 | F1G1 | 0 | F1G2 | F1G3 | N1 |
| 2923 | 0 | 0 | F1 | F1 | 0 | 0 | 0 | F1 | 0 | 0 | N1G2 | 0 |
| 2954 | 0 | K1G1 | F1 | 0 | 0 | 0 | 0 | N1G1 | 0 | G1 | F2G3 | F1 |
| 2987 | 0 | 0 | 0 | 0 | 0 | 0 | 0 | 0 | 0 | 0 | F1G1 | 0 |
| 2992 | F1G1 | K2F2 | F3G1 | F2G2 | 0 | K2G1 | 0 | F1 | 0 | 0 | F2G3 | N1 |
| 2994 | 0 | 0 | F1 | 0 | 0 | 0 | 0 | 0 | 0 | 0 | F3G1 | 0 |
| 2995 | 0 | 0 | F2 | 0 | F1 | 0 | 0 | 0 | G1 | 0 | F2G1 | G1 |
| 2996 | K3G3 | F2G2 | F3G2 | F3G2 | K2F1 | F2G2 | 0 | 0 | 0 | F1G1 | F3G2 | N1F2 |
| 2997 | F1 | G1 | F2 | F2G2 | F1 | F1 | 0 | F2G2 | G1 | F1G1 | F2G2 | F3 |
| 2998 | 0 | 0 | 0 | 0 | 0 | 0 | 0 | 0 | 0 | 0 | F1 | F1 |
| 2999 | 0 | 0 | 0 | 0 | 0 | 0 | 0 | 0 | 0 | 0 | F2 | 0 |
| 3000 | 0 | 0 | 0 | 0 | 0 | 0 | 0 | 0 | 0 | 0 | F2G1 | N1 |
| 3001 | 0 | 0 | 0 | 0 | 0 | 0 | 0 | 0 | 0 | 0 | F2G2 | G1 |
| 3002 | K4 | K4 | F3G3 | F1 | F2G1 | F1G2 | 0 | N1G1 | 0 | F1G1 | F3G3 | F1 |
| 3006 | F1F1 | F1G1 | F3G1 | F2G1 | G1 | F1G1 | 0 | F1 | 0 | 0 | F2G2 | 0 |
| 30017 | 0 | 0 | 0 | 0 | 0 | 0 | 0 | 0 | 0 | 0 | F1G1 | F1 |
| 3018 | K3G3 | G2 | F2G1 | F1 | F2G1 | F1G1 | 0 | 0 | 0 | 0 | F2G3 | 0 |
| 3019 | F1G2 | F2 | F2 | F2G1 | G1 | F1 | 0 | 0 | 0 | F1 | F3G2 | F2G2 |
| 3022 | F2G2 | F3G1 | F3G2 | F1G1 | F3G3 | F2G2 | 0 | N1 | N1 | N1G1 | F2G1 | 0 |
| 3023 | F2G2 | F3G3 | F2G2 | F2G2 | F2G1 | F1G1 | N1G1 | N1G2 | F1 | F1G1 | F2G2 | F2G1 |
| 3024 | 0 | 0 | 0 | 0 | 0 | 0 | 0 | 0 | 0 | 0 | F2G2 | 0 |
| 3025 | F1 | F1 | F1 | 0 | 0 | 0 | 0 | 0 | 0 | 0 | F1G1 | 0 |
| 3026 | F1 | G1 | F2 | 0 | 0 | 0 | 0 | 0 | 0 | 0 | F2G2 | 0 |
| 3027 | 0 | 0 | 0 | 0 | 0 | 0 | N1G1 | 0 | 0 | 0 | F2G1 | N2 |
| 3108 | F3G3 | F3G2 | F3G2 | F3G3 | F3G3 | F3G3 | N1G2 | F3G2 | N1F1 | F2G2 | F2G2 | F2G1 |
| 3109 | F3G3 | F3G2 | F3G3 | F3G3 | F2G2 | F2G2 | N2G1 | F3G2 | N1F1 | F2G1 | F2G2 | F2G1 |
| 3116 | F1 | F1 | F2 | F2G1 | F1G1 | F1 | N1 | N1G2 | 0 | N1 | F2G1 | N1F1 |
| 3137 | F3G2 | F2G2 | F3G2 | F3G3 | F2G1 | 0 | 0 | F3 | N1 | F2G1 | F2G2 | F3 |
| 3146 | F3G3 | F2G2 | F3G3 | F3G3 | F2G2 | F2G2 | N2G2 | N3G2 | F1 | N1G2 | N2G3 | F3 |
| 3147 | F1 | 0 | F1 | 0 | 0 | 0 | 0 | 0 | 0 | N1 | F2G2 | F2 |
| 3151 | F1 | F1G1 | F2G1 | F2G1 | F1 | F1 | N2G1 | F1 | F1 | F1 | F2G2 | F2 |
| 3152 | 0 | 0 | 0 | 0 | 0 | 0 | N1 | 0 | 0 | 0 | F1 | 0 |
| 3153 | F1 | 0 | F2 | F2G1 | F1G1 | F2G2 | G1 | F1 | 0 | 0 | F1 | F2 |
| 3158 | F1G1 | F2G1 | F3G1 | F3G1 | F2G2 | F3G3 | G1 | F3G1 | 0 | F2 | F2G3 | F2G1 |
| 3159 | F3G2 | F2G2 | F3G2 | F3G2 | F3G2 | F3G2 | N1G2 | F3G2 | F1 | F2 | N4 | F3G1 |
| 3160 | F2G2 | F1G1 | F3G1 | F3G2 | F2G2 | F2G2 | N1G2 | F2G1 | 0 | F2 | F2G2 | F3 |
| 3180 | F3G3 | F3G3 | F3G3 | K4 | F3G2 | F3G3 | N1G1 | F3G2 | F2 | F2 | F2G3 | F3 |
| 3181 | F3G3 | F3G2 | F3G3 | F3G3 | F2G2 | F3G2 | N1G2 | F3G2 | F2G1 | F2G1 | F2G2 | F3 |
| 3182 | F3G3 | F3G2 | F3g3 | F3G3 | F3G2 | F3G2 | N1G2 | F3G2 | F3G2 | F2G1 | F2G1 | F3 |
| 3183 | F3G3 | F2G2 | F3G3 | F3G3 | F2G2 | F2G2 | N2G2 | F3G3 | N1G1 | N2G2 | F2G3 | N2G1 |
| 3184 | F1 | 0 | F1 | 0 | 0 | 0 | 0 | 0 | 0 | F1 | F1 | 0 |
| 3185 | F2G2 | F1 | F2 | F3G2 | F1 | F1G1 | 0 | F1 | 0 | 0 | F2 | F2 |
| 3186 | 0 | 0 | 0 | 0 | 0 | 0 | 0 | F2 | 0 | 0 | F2 | F1 |
| 3187 | F1 | F1 | F2 | F2G1 | G1 | F1G1 | 0 | 0 | 0 | 0 | N2G2 | F2 |
| 3194 | F1G1 | F2 | F3G1 | F3G2 | F2 | F2G1 | F2G1 | F2G2 | F1 | F2 | F3G1 | F3 |
| 3195 | F2G2 | F2G1 | F3G1 | F3G3 | F2G1 | F2G1 | 0 | F2G1 | 0 | F1 | F3G1 | F3 |
| 3196 | F3G3 | F3G2 | F3G3 | F3G3 | F2G2 | F2G2 | N1G2 | F2G1 | 0 | F1 | F2G2 | F3 |
| 3210 | F2G2 | F2G2 | F3G3 | F3G3 | F2G2 | F3G2 | N2G3 | F3G2 | N1G2 | F1 | N3G3 | F3 |
| 3284 | F3G3 | F3G2 | F3G3 | F3G3 | F3G2 | F2G2 | F2G2 | F3G2 | F3G2 | F3 | F2G3 | F2 |
| 3285 | F1 | F1 | F2 | F2G1 | 0 | F2G1 | 0 | F3G2 | 0 | F1 | F3G2 | N1 |
| 3290 | F3G3 | F3G3 | F3G3 | F3G3 | F3G2 | F3G2 | N1G2 | F3G2 | F2G1 | F2G1 | F3G3 | F2 |
| 3349 | K4 | F3G3 | K4 | K3G3 | F3G2 | F3G3 | N1G2 | F3G3 | F1G1 | F3G2 | F3G2 | N1F1 |
| 3350 | F2G1 | F2G2 | F3G3 | F3G2 | F2G2 | F2G2 | F1G1 | F3G2 | F1G1 | F3G2 | F2G2 | F3G1 |
| 3352 | F3G2 | F2G2 | F3G3 | F3G2 | F2G2 | F3G2 | 0 | F3G2 | 0 | F1G3 | N3G2 | F2G1 |
| 3358 | K4 | F2G2 | F3G3 | F3G2 | F3G2 | F3G2 | F2G1 | F2G3 | F1 | C1G2 | F3G2 | F4 |
| 3577 | K4 | F3G3 | F3G3 | F3G2 | F3G3 | K4 | G2 | F3G2 | F1G2 | F2G1 | F3G3 | F3 |
| 3578 | K4 | F3G3 | K4 | F3G3 | F3G3 | F3G3 | F1G2 | F3G2 | F1G3 | F1G1 | F3G3 | F3 |
| 3579 | K4 | K4 | F3G3 | F3G3 | F3G3 | K4 | G2 | F3G2 | F1G2 | F2G1 | F3G3 | F3 |
| 3580 | K4 | F3G2 | F3G3 | F3G3 | F3G3 | F3G3 | G2 | F3G2 | F1G3 | F2G2 | F3G3 | F3 |
| 3581 | K4 | K4 | F3G3 | F3G3 | F3G2 | F3G3 | G2 | F3G2 | F1G2 | F2G1 | F3G3 | F3 |
| 3582 | F3G3 | F3G3 | K4 | F3G2 | F3G2 | F3G3 | G2 | F3G2 | F1G2 | F2G1 | F3G2 | F3 |
| 3676 | 0 | 0 | 0 | 0 | 0 | 0 | 0 | 0 | 0 | 0 | F1 | 0 |

-continued

EFFECTS ON VEGETATION

| | Pre-Emergent Effects | | | | | | Post-Emergent Effects | | | | | |
|---|---|---|---|---|---|---|---|---|---|---|---|---|
| Compd. No. | Digitaria sanguinalis | Celosia plumosa | Bromus inermis | Setaria italica | Raphanus sativus | Beta vulgaris | Setaria italica | Medicago sativa | Avena sativa | Raphanus sativus | Beta vulgaris | Lycopersicum esculentum |
| 3716 | F1G1 | F2 | F3G1 | F2G1 | F2G1 | F2G1 | F1G1 | F2 | — | G2N1F1 | F3G2 | F2N1G1 |

EXAMPLE 24

Seeds of *Soja max* were planted in 12 in. × 10 in. polystyrene foam trays, 3 inches deep, filled with greenhouse potting soil. Spray mixtures containing 1-(2-carbomethoxybenzoyl)-2-methyl-4-phenyl-3-thiosemicarbazide were prepared as in Example 23 and were applied to seeded trays at rates of 2, 1 and ½ lb per acre. The plants which subsequently emerged from treated soil had some leaves with 4 to 6 leaflets instead of the usual trifoliate leaves. Similar results are obtained by seed treatment at low rates of application, for instance, 0.0625 percent by weight of seed.

EXAMPLE 25

The use of many of the growth regulant compounds may be demonstrated by treatment of soybeans (*Soja max*) to increase the number of seed pods and by treating tomato plants (*Lycopersicum esculentum*) to increase fruit set. In an illustrative experiment, *Soja max* (Evans variety) and *Lycopersicum esculentum* (Tiny Tim variety) were grown in 4-inch pots (one plant per pot) filled with greenhouse potting soil (2 parts good top soil, 1½ parts builders sand, 1½ parts peat, fertilized with 5 lb of 12-12-6 fertilizer and 5 lb of finely ground limestone per cu. yd.). Aqueous spray formulations were prepared and the potted plants were sprayed at a spray volume of 40 gal. per acre (374 liters per hectare) and at application rates of 16, 4, and 1 oz. per acre. (1.12 kg, 280 g, and 70 g per hectare) The spray mixtures were prepared by dissolving the proper amount of growth regulant compound in 15 ml of acetone, adding 2 ml of a solvent-emulsifier mixture consisting of 60 wt. percent of a commercial polyethoxylated vegetable oil emulsifier (96 wt. percent active ingredient, Emulphor EL-719), 20 wt. percent xylene and 20 wt. percent deodorized kerosene, then bringing total volume up to 80 ml by addition of a 0.156 wt. percent aqueous solution of liquid non-ionic dispersant (90 wt. percent active trimethylnonyl polyethylene (glycol ether, Tergitol TMN-10). Two replicates were sprayed at all application rates. For comparative purposes, plants were also sprayed at 40 gal./acre with water. The number of seed pods and of fruit as percentage of arithmetic mean of the numbers on untreated plants was observed within approximately three weeks after spray treatment and the results are tabulated below. The extent of other growth regulatory effects observed on the plants was estimated on a scale of 0 to 10 (with 0=no other effect and 10=maximum effect) and is also recorded in the following table:

TABLE III
GROWTH REGULATING EFFECTS ON TWO SPECIES

| | | Soja max | | Lycopersicum esculentum | |
|---|---|---|---|---|---|
| Compound No. | Rate (oz/A) | Pod Count (Percent in Comparison to Untreated Plants) | Growth Regulating Effect (Average) | Fruit Count (Percent in Comparison to Untreated Plants) | Growth Regulating Effect (Average) |
| 597 | 16 | 171$^{a,c}$ | 9 | 400$^b$ | 9 |
| | 4 | 177$^{a,c}$ | 4.5 | 291 | 7 |
| | 1 | 151 | 2 | 436 | 1.5 |
| 1686 | 16 | 137 | 3 | 36 | 0 |
| | 4 | 120 | 0.5 | 36 | 0 |
| | 1 | 94 | 0 | 145 | 0 |
| 2005 | 16 | 169$^{a,c}$ | 9 | 255$^b$ | 9 |
| | 4 | 163$^{a,c}$ | 7.5 | 327 | 7.5 |
| | 1 | 160 | 3 | 364 | 3.5 |
| 2322 | 16 | 107 | 0.5 | 145 | 0 |
| | 4 | 103 | 0 | 218 | 0 |
| | 1 | 94 | 0 | 182 | 0 |
| 2324 | 16 | 97 | 0 | 73 | 1 |
| | 4 | 114 | 0 | 109 | 0 |
| | 1 | 97 | 0 | 36 | 0 |
| 2474 | 16 | 146$^{a,c}$ | 9 | 300$^a$ | 9 |
| | 4 | 154 | 7.5 | 382$^e$ | 8.5 |
| | 1 | 115 | 3.5 | 191 | 4.5 |
| 2481 | 16 | 157$^{a,c}$ | 8.5 | 136$^d$ | 7.5 |
| | 4 | 135 | 3.5 | 191 | 2.5 |
| | 1 | 104 | 1 | 164 | 0.5 |
| 2568 | 16 | 163$^{a,c}$ | 9 | 109$^{a,b}$ | 9 |
| | 4 | 166$^{a,c}$ | 5.5 | 327 | 7.5 |
| | 1 | 140 | 1.5 | 327 | 3.5 |
| 2584 | 16 | 120 | 2 | 145 | 0.5 |
| | 4 | 111 | 0 | 182 | 0 |
| | 1 | 103 | 0 | 145 | 0 |
| 2592 | 16 | 118 | 1.5 | 237$^c$ | 5 |
| | 4 | 115 | 1 | 245 | 1.5 |
| | 1 | 107 | 0 | 82 | 0 |
| 2622 | 16 | 115 | 3 | 327 | 1 |
| | 4 | 98 | 0 | 109 | 0 |
| | 1 | 95 | 0 | 136 | 0 |
| 2627 | 16 | 121 | 6.5 | 273 | 5.5 |
| | 4 | 104 | 1.5 | 245 | 1 |
| | 1 | 95 | 0 | 164 | 0 |
| 2628 | 16 | 159$^c$ | 8 | 273$^{d,e}$ | 8.5 |
| | 4 | 136 | 3.5 | 191 | 2.5 |
| | 1 | 95 | 0.5 | 136 | 0 |
| 2633 | 16 | 173$^a$ | 9 | 436$^{d,e}$ | 9 |
| | 4 | 138 | 3.5 | 245 | 3.5 |
| | 1 | 127 | 1 | 355 | 0.5 |
| 2634 | 16 | 173$^c$ | 8.5 | 300$^e$ | 8 |
| | 4 | 130 | 4.5 | 327 | 5 |
| | 1 | 113 | 0.5 | 164 | 0.5 |
| 2636 | 16 | 130$^{a,c}$ | 9 | 191$^{a,b,d}$ | 9 |
| | 4 | 133 | 4.5 | 436 | 4.5 |
| | 1 | 130 | 1.5 | 355 | 0.5 |
| 2637 | 16 | 147 | 6 | 327$^{a,d}$ | 9 |
| | 4 | 141 | 2.5 | 273$^e$ | 2.5 |
| | 1 | 104 | 1 | 245 | 0 |
| 2641 | 16 | 101 | 2 | 382$^d$ | 7.5 |
| | 4 | 101 | 0 | 245$^e$ | 1.5 |
| | 1 | 92 | 0 | 109 | 0 |
| 2668 | 16 | 144 | 8.5 | 300$^d$ | 8.5 |
| | 4 | 144 | 2.5 | 273$^e$ | 1.5 |
| | 1 | 124 | 0.5 | 327 | 0.5 |
| 2721 | 16 | 129$^{a,c}$ | 9 | 300$^a$ | 9 |
| | 4 | 129 | 5.5 | 245 | 5.5 |
| | 1 | 112 | 2.5 | 300 | 1 |
| 2722 | 16 | 143$^c$ | 7.5 | 218$^{d,e}$ | 7 |
| | 4 | 149 | 2.5 | 245 | 1.5 |
| | 1 | 126 | 0.5 | 300 | 0 |
| 2743 | 16 | 144 | 8 | 273$^d$ | 8.5 |

TABLE III-continued
GROWTH REGULATING EFFECTS ON TWO SPECIES

| | | Soja max | | Lycopersicum esculentum | |
|---|---|---|---|---|---|
| Compound No. | Rate (oz/A) | Pod Count (Percent in Comparison to Untreated Plants) | Growth Regulating Effect (Average) | Fruit Count (Percent in Comparison to Untreated Plants) | Growth Regulating Effect (Average) |
| | 4 | 170 | 2.5 | 245[c] | 3.5 |
| | 1 | 113 | 0 | 191 | 0.5 |
| 2744 | 16 | 124 | 7.5 | 245[d] | 9 |
| | 4 | 127 | 3 | 245[e] | 3 |
| | 1 | 104 | 0 | 382 | 1 |
| 2788 | 16 | 147[c] | 7.5 | 327[a,d] | 9 |
| | 4 | 130 | 2.5 | 355[e] | 4.5 |
| | 1 | 138 | 0 | 300 | 1.5 |
| 2790 | 16 | 191[a,c] | 9 | 364 | 8.5 |
| | 4 | 180[a,c] | 5 | 218 | 6.5 |
| | 1 | 169 | 2 | 255 | 3 |
| 2798 | 16 | 124 | 1.5 | 355 | 1 |
| | 4 | 101 | 0 | 82 | 0 |
| | 1 | 96 | 0 | 136 | 0 |
| 3116 | 16 | 132 | 3 | 191 | 1.5 |
| | 4 | 126 | 1 | 109 | 0 |
| | 1 | 110 | 0 | 164 | 0 |
| 3358 | 16 | 159[c] | 9 | 273[a,d] | 9 |
| | 4 | 156 | 5.5 | 300[e] | 2.5 |
| | 1 | 136 | 1.5 | 355 | 1 |
| 2598 | 16 | 111 | 8.5 | 150 | 3 |
| | 4 | 120 | 2 | 133 | 0 |
| | 1 | 111 | 0.5 | 150 | 0 |
| 2604 | 16 | 153 | 8.5 | 100 | 1.5 |
| | 4 | 147 | 4 | 167 | 0 |
| | 1 | 141 | 1 | 150 | 0 |
| 2605 | 16 | 123 | 5.5 | 133 | 1 |
| | 4 | 120 | 1.5 | 167 | 0.5 |
| | 1 | 120 | 0 | 117 | 0 |
| 2699 | 16 | 168 | 7 | 183 | 1.5 |
| | 4 | 159 | 2.5 | 67 | 0 |
| | 1 | 141 | 1 | 83 | 0 |
| 2701 | 16 | 138 | 8 | 83 | 2 |
| | 4 | 129 | 7 | 33 | 0.5 |
| | 1 | 123 | 1.5 | 67 | 0 |
| 2702 | 16 | 174 | 7.5 | 183 | 1.5 |
| | 4 | 174 | 5 | 100 | 0.5 |
| | 1 | 153 | 2 | 117 | 0 |
| 2707 | 16 | 159 | 7.5 | 100 | 0 |
| | 4 | 156 | 3 | 117 | 0 |
| | 1 | 108 | 0.5 | 83 | 0 |
| 2725 | 16 | 171 | 8.5 | 50 | 1 |
| | 4 | 177 | 4.5 | 150 | 0 |
| | 1 | 132 | 1 | 100 | 0 |
| 2726 | 16 | 147 | 8 | 33 | 0.5 |
| | 4 | 132 | 3.5 | 133 | 0 |
| | 1 | 99 | 0 | 83 | 0 |
| 2728 | 16 | 180 | 9 | 67 | 2 |
| | 4 | 159 | 6.5 | 67 | 0.5 |
| | 1 | 165 | 2.5 | 183 | 0 |
| 2389 | 16 | 159[c] | 6 | 286[b] | 8.5 |
| | 4 | 115 | 3.5 | 200 | 2.5 |
| | 1 | 105 | 1 | 229 | 1 |
| 2391 | 16 | 169[c] | 4.5 | 243[b] | 8.5 |
| | 4 | 150 | 1.5 | 271 | 5 |
| | 1 | 131 | 1 | 171 | 1.5 |
| 2487 | 16 | 169[c] | 6.5 | 229[b] | 8 |
| | 4 | 150 | 2.5 | 271 | 5 |
| | 1 | 131 | 1 | 171 | 1.5 |
| 2563 | 16 | 137 | 3.5 | 200 | 5 |
| | 4 | 108 | 1 | 157 | 0.5 |
| | 1 | 92 | 0 | 114 | 0 |
| 2570 | 16 | 150[a,c] | 9 | 171[b,d] | 8.5 |
| | 4 | 169 | 5.5 | 243 | 5.5 |
| | 1 | 143 | 2 | 271 | 2 |
| 2572 | 16 | 150 | 4.5 | 186 | 2.5 |
| | 4 | 108 | 1 | 100 | 0.5 |
| | 1 | 96 | 0 | 57 | 0 |
| 2574 | 16 | 134 | 6 | 143 | 2 |
| | 4 | 127 | 2.5 | 214 | 0.5 |
| | 1 | 96 | 0 | 186 | 0 |
| 2879 | 16 | 137 | 3.5 | 186 | 2.5 |
| | 4 | 140 | 1 | 143 | 0.5 |
| | 1 | 108 | 0 | 129 | 0 |
| 2996 | 16 | 137 | 2.5 | 171 | 3 |
| | 4 | 150 | 1 | 171 | 0.5 |
| | 1 | 124 | 0 | 114 | 0 |
| 3017 | 16 | 105 | 2.5 | 143 | 1 |
| | 4 | 99 | 0 | 186 | 0 |
| | 1 | 96 | 0 | 86 | 0 |
| 3018 | 16 | 108 | 3.5 | 129 | 2 |
| | 4 | 105 | 0.5 | 157 | 0 |
| | 1 | 115 | 0 | 129 | 0 |
| 3350 | 16 | 131[a,c] | 9 | 129[d] | 7.5 |
| | 4 | 150 | 4.5 | 243 | 2 |
| | 1 | 118 | 1.5 | 214 | 2 |
| 3022 | 16 | 124 | 3.5 | 143 | 2.5 |
| | 4 | 108 | 0.5 | 129 | 0 |
| | 1 | 92 | 0 | 114 | 0 |
| 3023 | 16 | 127 | 4.5 | 157 | 3.5 |
| | 4 | 124 | 1.5 | 143 | 1 |
| | 1 | 99 | 0 | 157 | 0 |
| 2418 | 16 | 150 | 3.5 | 103 | 3.5 |
| | 4 | 125 | 1 | 169 | 1 |
| | 1 | 125 | 0 | 94 | 0 |

Footnotes
[a]Injurious
[b]Malformed fruit
[c]Smaller pods
[d]Stimulated growth
[e]Pear-shaped fruit

EXAMPLE 26

Several species of plants were grown in potting soil in four-inch pots in the greenhouse. Aqueous spray formulations containing 1-(2-carbomethoxybenzoyl)-2-methyl-4-phenyl-3-thiosemicarbazide were prepared and the potted plants were sprayed at a spray volume of 40 gallons per acre (374 liters per hectare) and application rates of 16, 4, 1 and ¼ oz. per acre (1.12 kg, 280 g, 70 g and 17.5 g per hectare). The spray mixtures were prepared by dissolving the proper amount of 1-(2-carbomethoxybenzoyl)-2-methyl-4-phenyl-3-thiosemicarbazide in 15 ml of acetone, adding 2 ml of a solvent-emulsifier mixture consisting of 60 wt. percent of a commercial polyethoxylated vegetable oil emulsifier (96 wt. percent active ingredient, Emulphor EL-719), 20 wt. percent xylene and 20 wt. percent deodorized kerosene, then bringing total volume up to 80 ml by addition of a 0.156 wt. percent aqueous solution of liquid non-ionic dispersant (90 wt. percent active trimethylnonyl polyethylene glycol ether, Tergitol TMN-10). Two replicates were sprayed at all application rates. For comparative purposes, plants were also sprayed at 40 gal./acre with a corresponding solvent-surfactant mixture dispersed in water.

The following growth regulating effects were observed and evaluated:
Epinasty
Drooping leaves
Stunting
Formative effects on new growth The total of all effects was scored on a scale of 0=no effect to 10=maximum effect. The results are summarized in the following table.

TABLE IV

| Plant species, variety and stage of growth | Appl'n rate (oz/A.) | Score | Description of effects |
|---|---|---|---|
| *Setaria italica* | 16 | 0 | No visible effect |
| 10–12 inches, 6–7 leaves | 4 | 0 | |
| | 1 | 0 | |
| | ¼ | 0 | |
| *Sorghum vulgare* | 16 | 0 | No visible effect |
| DeKalb E-57 | 4 | 0 | |
| 12–15 in., 6 leaves | 1 | 0 | |
| | ¼ | 0 | |
| *Zea mays,* DeKalb XL-373 | 16 | 0 | No visible effect |
| 16–18 in., 6–7 leaves | 4 | 0 | |
| | 1 | 0 | |
| | ¼ | 0 | |
| *Hordeum vulgare,* Larker | 16 | 0 | No visible effect |
| 10–12 in., 4–5 leaves | 4 | 0 | |
| | 1 | 0 | |
| | ¼ | 0 | |
| *Oryza sativa,* Labelle | 16 | 0 | No visible effect |
| 6–8 in., 3–4 leaves | 4 | 0 | |
| | 1 | 0 | |
| | ¼ | 0 | |
| *Soja max,* Williams | 16 | 9 | At 16 oz. new leaves much smaller. |
| 9–11 in., 2 trifoliates | 4 | 9 | Epinasty on stems, formative effect |
| plus ½ of next leaf | 1 | 4 | on leaves, plants darker green in |
| | ¼ | 1 | color. |
| *Gossypium herbaceum,* | 16 | 3 | Leaves were in vertical position, |
| Stoneville 213 | 4 | 0 | rather than horizontal. |
| 8–10 in., 3 true leaves | 1 | 0 | |
| | ¼ | 0 | |
| *Arachis hypogaea,* | 16 | 3 | Leaves drooping, slight epinasty. |
| Florunner | 4 | 0 | |
| 6–8 in., 6 leaves | 1 | 0 | |
| | ¼ | 0 | |
| *Medicago sativa,* Kansas | 16 | 8 | Epinasty, formative effect on new |
| Common | 4 | 3 | growth; many new stems at base with |
| | 1 | 0 | formative effects. |
| | ¼ | 0 | |
| *Linum usitatissimum,* Linott | 16 | 2 | Slight increase in axillary growth. |
| 6–7 in., 26–32 leaves | 4 | 0 | |
| | 1 | 0 | |
| | ¼ | 0 | |
| *Beta vulgaris,* Great | 16 | 8 | Formative effect (rolling) of |
| Western | 4 | 5 | leaves, stunting, new growth |
| 5–6 in., 4 true leaves | 1 | 4 | inhibited. |
| | ¼ | 0 | |
| *Brassica napus,* Torch | 16 | 7 | Formative effect on new growth. |
| 5–6 in., 4–5 true leaves | 4 | 4 | Stunting. |
| | 1 | 2 | |
| | ¼ | 0 | |
| *Phaseolus vulgaris,* UI-114 | 16 | 9 | Epinasty, drooping of leaves, |
| 14–16 in., 3–4 trifoliate | 4 | 8 | formative effect on new |
| leaves | 1 | 5 | growth. Stunting at higher |
| | ¼ | 3 | application rates. |
| *Phaseolus vulgaris,* Topcrop | 16 | 9 | Epinasty, drooping of leaves, |
| 11–13 in., 3 trifoliate | 4 | 9 | formative effect on new growth, |
| leaves | 1 | 8 | earlier set of beans, stunting at |
| | ¼ | 3 | higher application rates. |
| *Cucumis sativus,* Marketer | 16 | 3 | At 16 and 4 oz. per A. new growth |
| 11–13 in., 4 true leaves | 4 | 0 | stopped. |
| | 1 | 0 | |
| | ¼ | 0 | |
| *Cucumis melo,* Hearts of | 16 | 2 | Stunting, axillary growth |
| Gold | 4 | 0 | inhibited. |
| 9–11 in., 3–4 true leaves | 1 | 0 | |
| | ¼ | 0 | |
| *Citrullus vulgaris,* Congo | 16 | 1 | Slight increase in fruit set. |
| 8–10 in., 3 true leaves | 4 | 0 | Vines 18 in. in length had melons. |
| | 1 | 0 | |
| | ¼ | 0 | |
| *Raphanus sativus,* Scarlet | 16 | 2 | Formative effect on new leaves at |
| Globe 5–7 in. 4–5 true | 4 | 1 | highest rates. |
| leaves | 1 | 0 | |
| | ¼ | 0 | |
| *Caucus carota,* Gold Pak | 16 | 2 | Formative effect on leaves. |
| 3–4 in., 3–4 true leaves | 4 | 1 | |
| | 1 | 0 | |
| | ¼ | 0 | |
| *Allium cepa,* Yellow | 16 | 0 | No visible effect. |
| Bermuda 5–6 in., 2 leaves | 4 | 0 | |
| | 1 | 0 | |

TABLE IV-continued

| Plant species, variety and stage of growth | Appl'n rate (oz/A.) | Score | Description of effects |
|---|---|---|---|
| | 1/4 | 0 | |
| Beta vulgaris, Detroit | 16 | 9 | Severe drooping of leaves and |
| Dark Red | 4 | 9 | stunting. Leaves rolled together. |
| 4-5 in., 4-5 true leaves | 1 | 9 | |
| | 1/4 | 8 | |
| Lactuca sativa, Black | 16 | 0 | No visible effect. |
| Seeded Simpson | 4 | 0 | |
| | 1 | 0 | |
| | 1/4 | 0 | |
| Lycopersicum esculentum, | 16 | 9 | Formative effect on new leaves at |
| Tiny Tim | 4 | 8 | all application rates, epinasty, |
| 7-8 in., 6-8 true leaves, | 1 | 8 | drooping of leaves within 24 hours, |
| blooming (6 weeks old) | 1/4 | 7 | much earlier and increased fruit set (8-10 tomatoes versus 1-2 for untreated plants) |

EXAMPLE 27

Seeds of Williams variety *Soja max* were planted in a field in Missouri on May 15th. The compound 1-(2-carbomethoxybenzoyl)-2-methyl-4-phenyl-3-thiosemicarbazide was applied at five different rates, (16, 4, 1, 1/4 and 1/16 oz. per acre) at four different times, July 7th, July 18th, July 27th and August 8th. Each application rate was replicated four times in four different soil fertilization programs. On July 15th there was severe hail damage to the plots in a spotty, non-uniform pattern which made it impossible to score the final results quantitatively. It was observed on July 18th that in damaged areas, some of the best plants containing the most seed pods had received the most severe injuries. An inspection of plants in less damaged areas on August 8th indicated that the application of 4 oz. per acre of growth regulant on July 18th had increased the size and number of seed pots, particularly in the upper one-third of the plants. Counts showed an average of 109 seed pods on the treated plants versus 86 pods on untreated plants. At the time of spraying the plants had been 30 to 33 inches tall, in bloom and with 8 to 10 small pods on each plant. On September 7th it was observed that both treated and untreated plots had shown substantial recovery from hail damage. Although many stems had been bent or broken off, new growth had occurred and more seed pods had set. Treated plants, particularly those treated at 4, 1 and 1/4 oz. per acre were still green and had many well-filled pods all the way to the top of each plant. Untreated plants had begun to change color, indicating that growth of beans had ceased and the ripening stage was beginning.

In a similar test plot of Williams variety of *Soja max* in Kansas, which was planted on May 30th and was treated with the same compound on July 28th at 1 oz. and 4 oz. per acre, a substantial increase in pod set was observed in August. On September 5th the plants were mature and had stopped blooming and setting pods. A count was made of pods and seeds on the best of three untreated plants selected at random and on randomly selected individual treated plants. Results were as follows:

| Application rate, oz. per acre | 0 | 1 | 4 |
|---|---|---|---|
| Number of pods, one plant | 54 | 81 | 64 |
| Number of beans, | 132 | 212 | 181 |

| -continued | | | |
|---|---|---|---|
| Application rate, oz. per acre | 0 | 1 | 4 |
| one plant Plant increase | 0 | 61% | 37% |

In another test plot in Kansas about 135 miles south of the one discussed above, seeds of *Soja max* of the York variety were planted in drilled rows 36 cm. apart on July 10th, after the harvesting of wheat in the area. The plants were sprayed with 1-(2-carbomethoxybenzoyl)-2-methyl-4-phenyl-3-thiosemicarbazide at rates of 1, 2 and 4 oz. per acre on August 24th. The plants at the time of spraying were about 21 inches (53 cm.) high and were in budding and blooming stage. On September 7th the plants were examined and were found to be still green and almost through with budding and blooming. Counts were made on groups of five randomly selected plants from each treatment of the number of pods set on plants. Results were as follows:

| Application rate, oz. per acre | 0 | 1 | 2 | 4 |
|---|---|---|---|---|
| Total No. of pods, 5 plants | 109 | 184 | 183 | 177 |
| Percent Increase | 0 | 69% | 67% | 62% |

EXAMPLE 28

Among the compounds referred to in the foregoing tables, interesting and useful growth regulating effects are also observed on other species. For example, tillering of *Avena sativa* (oats) and in some instances also of *Triticum aestivum* (wheat) was observed with resulting increase in number of seed heads by compounds numbered as follows:

| | | |
|---|---|---|
| 2790 | 2882 | 3146 |
| 2822 | 2883 | 3180 |
| 2844 | 2885 | 3181 |
| 2845 | 3108 | 3210 |
| 2854 | 3109 | 3284 |

Among the preferred compounds of this invention are those wherein R is

m is 0, $R^3$ is hydrogen or $C_1$-$C_4$ alkyl, $R^4$ is hydrogen and Ar is phenyl or benzyl, either of which can be substituted as shown in formula I. A more preferred class of compounds are those wherein Ar is phenyl or phenyl monosubstituted with fluoro, chloro, bromo, methyl, benzyloxy, methoxy or triifluoromethyl. The most preferred $R^3$ substituent is methyl.

Another preferred class of compounds are those compounds of formula I wherein R is

m is 0, $R^3$ is hydrogen or methyl, $R^4$ is hydrogen. Ar is

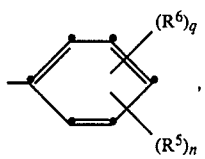

n is 0 or 1 and q is 0, or an agriculturally acceptable salt or ester thereof.

Still another preferred class of compounds are those of the formula

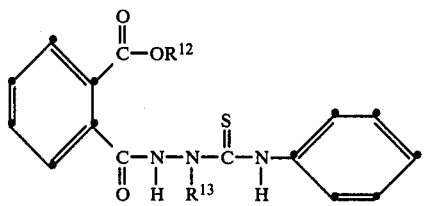

wherein
$R^{12}$ is hydrogen, lower alkyl or an agriculturally-acceptable cation and
$R^{13}$ is hydrogen or lower alkyl.

A still further preferred class of compounds are those of the formula

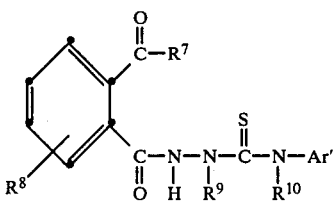

wherein
$R^7$ is —OH, —$OR^{11}$, —OA or —$NR'''R''''$;
$R^{11}$ is $C_1$-$C_{18}$ alkyl, $C_1$-$C_8$ haloalkyl or $C_3$-$C_8$ alkoxyalkyl;
A is $Na^+$, $K^+$, $Li^+$, $NH_4^+$ or other agriculturally acceptable cation;
$R'''$ and $R''''$ are hydrogen or methyl;
$R^8$ is hydrogen, methyl, nitro, chloro or fluoro;
$R^9$ is hydrogen, $C_1$-$C_4$ alkyl, $C_3$-$C_4$ alkenyl containing no $\alpha,\beta$ unsaturation or benzyl;
Ar' is naphthyl, anthranyl or phenanthryl, or benzyl which may have one of methyl, methoxy, bromo, chloro, fluoro and tri fluoromethyl substituents thereon, or phenyl which may have one to three of methyl, methoxy, bromo, chloro, fluoro and trifluoromethyl substituents thereon provided that both ortho positions of phenyl are not substituted by methyl; and
$R^{10}$ is hydrogen or $C_1$-$C_3$ alkyl.

A still further class of preferred compounds are those wherein R is —$CH_2OH$, $R^3$ is hydrogen or $C_1$-$C_4$ alkyl, m is 0, $R^4$ is hydrogen and Ar is naphthyl or a group having one of the following formulae:

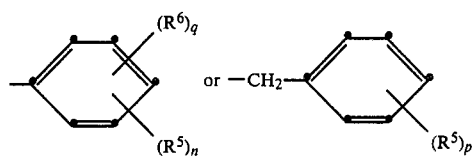

By the term "agriculturally-acceptable salts and esters" is meant salts and esters of the compounds of this invention which may be used in plant growth regulation in the same manner as the parent compounds to achieve the same effects. Such salts and esters do not adversely affect the activity of the compounds nor do they have a substantial adverse effect upon the plants to which they are applied for the purpose of achieving a beneficial effect.

Among such agriculturally-acceptable esters are those prepared from primary and secondary alkanols, such as those containing from one to about eighteen carbon atoms, haloalkanols containing from one to about eight carbon atoms, alkoxyalkanols containing about three to about eight carbon atoms and arylalkanols containing from seven to about ten carbon atoms. Exemplary of acceptable alkanols are methanol, ethanol, isopropanol, neopentyl alcohol, undecanol, hexadecanol, and octadecanol. Among exemplary haloalkanols are chloroethanol, 3-bromopropanol and chlorohexanol. Useful alkoxyalkanols include methoxyethanol, ethoxyethanol, butoxyethanol and such alkoxyalkoxyalkanols as butoxyethoxyethanol and ethoxyethoxyethanol. Suitable arylalkanols include benzyl alcohol and phenethanol.

Salts of the compounds of this invention include metal salts, ammonium salts, quaternary ammonium salts and amine salts. Numerous examples of such salts are found in the Examples of this specification.

We claim:
1. A compound of the formula

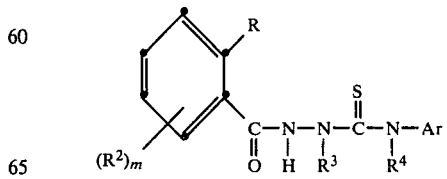

wherein
R is

R[1] is —OH;
m is 0;
R[3] is methyl;
R[4] is hydrogen;
Ar is naphthyl or a group having the following formula:

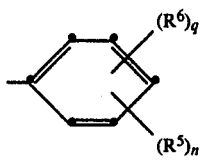

each R[5] independently is $C_1$-$C_4$ alkyl chloro,
bromo, fluoro, nitro, $C_1$-$C_3$ alkoxy of
$C_1$-$C_3$ alkylthio, provided that both ortho positions are not substituted by alkyl;
R[6] is carbethoxy, phenoxy, benzyloxy, phenyl or dimethylamino;
n is 0, 1, or 2;
q is 0;
the sum of n plus q does not exceed 2;
or an agriculturally-acceptable salt or ester thereof.

2. The sodium salt of the compound of claim 1.
3. The ammonium salt of the compound of claim 1.
4. The methyl ester of the compound of claim 1.
5. The ethyl ester of the compound of claim 1.
6. The hexadecyl ester of the compound of claim 1.
7. The compound of claim 1 wherein R is

m is 0, R[3] is methyl, R[4] is hydrogen and Ar is 4-bromophenyl, or an agricuturally-acceptable salt or ester thereof.

8. The methyl ester of the compound of claim 7.
9. The compound of claim 1 wherein R is

m is 0, R[3] is methyl, R[4] is hydrogen and Ar is 3-methylphenyl, or an agriculturally-acceptable salt or ester thereof.

10. The methyl ester of the compound of claim 9.
11. The compound of claim 1 wherein R is

m is 0, R[3] is methyl, R[4] is hydrogen and Ar is 4-methylphenyl, or an agriculturally-acceptable salt or ester thereof.

12. The methyl ester of the compound of claim 11.
13. The compound of claim 1 wherein R is

m is 0, R[3] is methyl, R[4] is hydrogen and Ar is 2-fluorophenyl, or an agriculturally-acceptable salt or ester thereof.

14. The methyl ester of the compound of claim 10.
15. The compound of claim 1 wherein R is

m is 0, R[3] is methyl, R[4] is hydrogen and Ar is 4-chlorophenyl, or an agriculturally-acceptable salt or ester thereof.

16. The methyl ester of the compound of claim 15.
17. The compound of claim 1 wherein R is

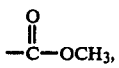

m is 0, R[3] is methyl, R[4] is hydrogen and Ar is 2-chlorophenyl, or an agriculturally-acceptable salt or ester thereof.

18. The compound of claim 1 wherein R is

m is 0, R[3] is methyl, R[4] is hydrogen and Ar is 3-trifluoromethylphenyl, or an agriculturally-acceptable salt or ester thereof.

19. The methyl ester of the compound of claim 18.
20. The potassium salt of the composition of claim 1.
21. A plant growth regulating composition comprising an agriculturally-acceptable adjuvant and an effective amount of a compound of claim 1.
22. A plant growth regulating composition comprising an agriculturally-acceptable adjuvant and an effective amount of a compound of claim 1 wherein n is zero.
23. A plant growth regulating composition comprising an agriculturally-acceptable adjuvant and an effective amount of the compound of claim 1 wherein Ar is phenyl.
24. A plant growth regulating composition comprising an agriculturally-acceptable adjuvant and an effective amount of the compound of claim 4.

* * * * *

UNITED STATES PATENT OFFICE
CERTIFICATE OF CORRECTION

Patent No. 4,462,821　　　　　　　　　Dated July 31, 1984

Inventor(s) Jerry L. Rutter and James L. Ahle

It is certified that error appears in the above-identified patent and that said Letters Patent are hereby corrected as shown below:

Col. 4, line 20, "to reflux" should read --at reflux--;
Col. 10, No. 2574, "3-chloro-methyl" should read --3-chloro-4-methyl--;
Col. 18, No. 3146, M.P.°C., "133-14 135°" should read --133-135°--;
Col. 25, line 8, "dying" should read --drying--;
Col. 28, line 25, "174 inch of soil" should read --1/4 inch of soil--;
Col. 29, Comp. 2432, under Raphanus sativus, "F3G3" should read --F3G1--;
Col. 30, Comp. 2325, last column, "F33" should read --F3--;
Col. 31, Comp. 2635, under Setaria italica, insert --F3G3--, shifting the remaining figures for Comp. 2635 one column to the right;
Col. 31, Comp. 2701, first column, "F1G1" should read --F2G1--;
Col. 32, Comp. 2844, under Beta vulgaris, "F362" should read --F2G3--;
Col. 34, Comp. 2879, under Medicago sativa, insert --F1--, shifting the remaining figures for Comp. 2879 one column to the right;
Col. 33, below Comp. 3006, "30017" should read --3017--;
Col. 33, Comp. 3182, under Bromus inermis, "F3g3" should read --F3G3--;
Col. 41, line 37, "seed pots" should read --seed pods--;
Col. 44, line 18, "$(R^6)_q$" should read --$(R^6)_p$--;
Col. 45, line 23 (cl. 1), "alkoxy of" should read --alkoxy or--;
Col. 46, line 18 (cl. 14), "claim 10" should read --claim 13--.

Signed and Sealed this

*Twenty-fourth* Day of *September 1985*

[SEAL]

Attest:

DONALD J. QUIGG

Attesting Officer

*Commissioner of Patents and Trademarks—Designate*